US010758209B2

(12) United States Patent
Boctor et al.

(10) Patent No.: US 10,758,209 B2
(45) Date of Patent: Sep. 1, 2020

(54) PHOTOACOUSTIC TRACKING AND REGISTRATION IN INTERVENTIONAL ULTRASOUND

(71) Applicant: The Johns Hopkins University, Baltimore, MD (US)

(72) Inventors: Emad M. Boctor, Baltimore, MD (US); Russell H. Taylor, Severna Park, MD (US); Jin U. Kang, Ellicott City, MD (US)

(73) Assignee: The Johns Hopkins University, Baltimore, MD (US)

( * ) Notice: Subject to any disclaimer, the term of this patent is extended or adjusted under 35 U.S.C. 154(b) by 1392 days.

(21) Appl. No.: 14/381,374

(22) PCT Filed: Mar. 11, 2013

(86) PCT No.: PCT/US2013/030273
§ 371 (c)(1),
(2) Date: Aug. 27, 2014

(87) PCT Pub. No.: WO2013/134782
PCT Pub. Date: Sep. 12, 2013

(65) Prior Publication Data
US 2015/0031990 A1 Jan. 29, 2015

Related U.S. Application Data

(60) Provisional application No. 61/608,910, filed on Mar. 9, 2012.

(51) Int. Cl.
*A61B 8/08* (2006.01)
*A61B 5/00* (2006.01)
(Continued)

(52) U.S. Cl.
CPC .......... *A61B 8/5261* (2013.01); *A61B 5/0084* (2013.01); *A61B 5/0095* (2013.01);
(Continued)

(58) Field of Classification Search
CPC combination set(s) only.
See application file for complete search history.

(56) References Cited

U.S. PATENT DOCUMENTS 4,896,673 A 1/1990 Rose et al.
5,551,429 A 9/1996 Fitzpatrick et al.
(Continued)

FOREIGN PATENT DOCUMENTS

CA 2108098 A1 4/1994
EP 0998238 A1 5/2000
(Continued)

OTHER PUBLICATIONS

Arun et al., "Least-Squares Fitting of Two 3-D Point Sets", *IEEE Transactions on Pattern Analysis and Machine Intelligence*, vol. 9-5, pp. 698-700, 1987.
(Continued)

*Primary Examiner* — James M Kish
(74) *Attorney, Agent, or Firm* — Harrity & Harrity, LLP

(57) ABSTRACT

An intraoperative registration and tracking system includes an optical source configured to illuminate tissue intraoperatively with electromagnetic radiation at a substantially localized spot so as to provide a photoacoustic source at the substantially localize spot, an optical imaging system configured to form an optical image of at least a portion of the tissue and to detect and determine a position of the substantially localized spot in the optical image, an ultrasound imaging system configured to form an ultrasound image of at least a portion of the tissue and to detect and determine a position of the substantially localized spot in the ultrasound
(Continued)

image, and a registration system configured to determine a coordinate transformation that registers the optical image with the ultrasound image based at least partially on a correspondence of the spot in the optical image with the spot in the ultrasound image.

24 Claims, 15 Drawing Sheets

(51) Int. Cl.
*A61B 8/00* (2006.01)
*A61B 34/20* (2016.01)
*A61B 90/00* (2016.01)
*A61B 8/14* (2006.01)
*A61B 6/03* (2006.01)
*A61B 6/00* (2006.01)
*A61B 90/30* (2016.01)

(52) U.S. Cl.
CPC .............. *A61B 8/0841* (2013.01); *A61B 8/14* (2013.01); *A61B 8/4254* (2013.01); *A61B 8/445* (2013.01); *A61B 8/4416* (2013.01); *A61B 8/483* (2013.01); *A61B 34/20* (2016.02); *A61B 90/361* (2016.02); *A61B 90/37* (2016.02); *A61B 6/032* (2013.01); *A61B 6/5247* (2013.01); *A61B 2034/2063* (2016.02); *A61B 2034/2065* (2016.02); *A61B 2090/306* (2016.02); *A61B 2090/364* (2016.02); *A61B 2090/365* (2016.02); *A61B 2090/371* (2016.02); *A61B 2090/373* (2016.02); *A61B 2090/378* (2016.02); *A61B 2090/3937* (2016.02); *A61B 2090/3945* (2016.02)

(56) References Cited

U.S. PATENT DOCUMENTS

| | | | |
|---|---|---|---|
| 6,160,835 A * | 12/2000 | Kwon | B23K 26/06 219/121.68 |
| 6,178,340 B1 | 1/2001 | Svetliza | |
| 2004/0105580 A1* | 6/2004 | Hager | G06K 9/32 382/154 |
| 2004/0147810 A1* | 7/2004 | Mizuno | A61B 5/0068 600/178 |
| 2005/0049486 A1 | 3/2005 | Urquhart et al. | |
| 2008/0071172 A1 | 3/2008 | Bruck et al. | |
| 2008/0123083 A1* | 5/2008 | Wang | A61B 5/0091 356/73 |
| 2009/0015626 A1 | 1/2009 | Murayama et al. | |
| 2009/0015826 A1 | 1/2009 | Ramanujam et al. | |
| 2009/0018445 A1* | 1/2009 | Schers | A61B 8/0875 600/437 |
| 2009/0054763 A1* | 2/2009 | Wang | A61B 5/0059 600/425 |
| 2009/0187099 A1 | 7/2009 | Burcher et al. | |
| 2009/0322608 A1 | 12/2009 | Adams et al. | |
| 2010/0168561 A1 | 7/2010 | Anderson | |
| 2010/0245769 A1* | 9/2010 | Zhang | A61B 5/0059 351/219 |
| 2010/0331662 A1 | 12/2010 | Fukutani et al. | |
| 2011/0130659 A1 | 6/2011 | Cinquin et al. | |
| 2011/0172530 A1 | 7/2011 | Slayton et al. | |
| 2012/0253200 A1 | 10/2012 | Stolka et al. | |
| 2013/0168532 A1* | 7/2013 | Schmid | G01N 21/1702 250/205 |
| 2014/0121502 A1 | 5/2014 | Vignon et al. | |
| 2014/0378796 A1 | 12/2014 | Chen et al. | |
| 2016/0038119 A1 | 2/2016 | Desjardins et al. | |
| 2016/0228090 A1 | 8/2016 | Boctor et al. | |

FOREIGN PATENT DOCUMENTS

| | | | |
|---|---|---|---|
| EP | 1795142 A1 | 6/2007 | |
| EP | 2143038 A1 | 1/2010 | |
| WO | WO-1996010949 A1 | 4/1996 | |
| WO | WO-1998040760 A1 | 9/1998 | |
| WO | WO-2002024094 A2 | 9/2001 | |
| WO | WO-2002000093 A2 | 1/2002 | |
| WO | WO-2005039391 A2 | 5/2005 | |
| WO | WO-2007115825 A1 | 10/2007 | |
| WO | WO-2008004222 A2 | 1/2008 | |
| WO | WO-2009027277 A2 | 3/2009 | |
| WO | WO 2011/063266 * | 5/2011 | .............. A61B 6/03 |
| WO | WO-2011/100753 A2 | 8/2011 | |
| WO | WO-2012033552 A1 | 3/2012 | |

OTHER PUBLICATIONS

Bhayani et al., "Robotic assisted laparoscopic partial nephrectomy for suspected renal cell carcinoma: retrospective review of surgical outcomes of 35 cases", BMC Surgery, vol. 8-16, 2008.

Boctor et al., "Brachytherapy Seed Localization Using Combined Photoacoustic and Ultrasound Imaging (Abstract 7629-49)", in SPIE Medical Imaging Conference San Diego, 2010, p. 203.

Boctor et al., "Three-dimensional ultrasound-guided robotic needle placement: an experimental evaluation", Int. J. of Medical Robotics and Computer Assisted Surgery, vol. 4-2, pp. 180-191, 2008.

Boctor et al., A Novel Closed Form Solution for Ultrasound Calibration. In International Symposium on Biomedical Imaging, Arlington, 527-530 (2004).

Bopp et al., "An Orientation and Calibration Method for Non-Topographic Applications", Photogrammetric Engineering and Remote Sensing, vol. 44-9, pp. 1191-1196, Sep. 1978.

Cannon et al., "Real-Time Three-Dimensional Ultrasound for Guiding Surgical Tasks", Computer Aided Surgery, vol. 8-2, pp. 82-90, 2003.

Cheng et al., "Direct 3D Ultrasound to Video Registration Using the Photoacoustic Effect", in Medical Image Computing and Computer-Assisted Intervention (MICCAI), Nice, Oct. 2012. p. (accepted).

Cheung et al., "Fused Video and Ultrasound Images for Minimally Invasive Partial Nephrectomy: A Phantom Study", in Medical Image Computing and Computer-Assisted Interventions (MICCAI), Beijing, Sep. 20-24, 2010. pp. 408-415.

Choti, "Surgical Management of Hepatocellular Carcinoma: Resection and Ablation", Journal of Vascular and Interventional Radiology, vol. 13-9 Pt 2, pp. S197-S203, Sep. 2002.

Estepar et al., "Towards Real Time 2D to 3D Registration for Ultrasound-Guided Endoscopic and Laparoscopic Procedures", International Journal of Computer Assisted Radiology and Surgery, vol. 4-6, pp. 549-560, 2009.

Estepar et al., "Towards Scarless Surgery: An System for Transgastric Access Procedures", in Medical Image Computing and Computer Assisted Intervention, 2006. pp. 445-453.Endoscopic-Ultrasound Navigation.

Foroughi et al., "Tracked Ultrasound Elastography (TrUE)", Medical Image Computing and Computer Assisted Intervention, vol. 13—Pt 2, pp. 9-16, 2010.

Guthart et al., "The Intuitive Telesurgery System: Overview and Application", in Proc. of the IEEE International Conference on Robotics and Automation (ICRA2000), San Francisco, 2000, pp. 618-621.

Hager et al., "The XVision System: A General-Purpose Substrate for Portable Real-Time Vision Applications", Computer Vision and Image Understanding, vol. 69-1, pp. 23-37, Jan. 1998.

Haralick, "2D-3D pose estimation", in Int Conf on Pattern Recognition (ICPR), Nov. 14-17, 1988. pp. 385-391.

Harrison et al., "Coregistered photoacoustic-ultrasound imaging applied to brachytherapy", I Biomnedical Optics, vol. 16-8, Aug. 2011.

Hoelen et al., Three-dimensional photoacoustic imaging of blood vessels in tissue. Optics letters 23(8), 648-650 (1998).

(56) References Cited

OTHER PUBLICATIONS

Horn et al., "Closed-form solution of absolute orientation using orthonormal matrices", *J Optical Cos Am*, vol. 5-, pp. 1127-1135, 1988.
Kang et al., "OpenITGLinkMUSiiC: A Standard Communications Protocol for Advanced Ultrasound Research", *The MIDAS Journal*, 2011.
Kang et al., "Ultrasound Imaging Software Framework for Real-Time Monitoring of Acoustic Ablation Therapy", in *SPIE Medical Imaging*, San Diego, 2012.
Kang et al., Software framework of a real-time pre-beamformed RF data acquisition of an ultrasound research scanner, in Medical Imaging 2012: Visualization, Image-Guided Procedures, and Modeling, San Diego, Feb. 4-9, 8320, 83201F (2012).
Kazanzides et al., "The Surgical Assistant Workstation (SAW) in Minimally-Invasive Surgery and Microsurgery", in International Workshop on Systems and Architectures for Computer Assisted Interventions, Beijing, Sep. 24, 2010.
Keil et al., "Ultrasound and CT Registration Quality: Elastography vs. Classical B-Mode", in ISBI, 2009. pp. 967-970.
Kim et al., "Handheld array-based photoacoustic probe for guiding needle biopsy of sentinel lymph nodes", *Journal of Biomedical Optics*, vol. 154-, p. 046010, Jul./Aug. 2010.
Choti et al., "Robotically Assisted Radiofrequency Ablation of Liver Cancer", *IHPBA*, 2002.
Kolkman et al., In vivo photoacoustic imaging of blood vessels with a pulsed laser diode. Lasers in medical science 21(3), 134-139 (2006).
Ku et al., "Thermoacoustic and Photoacoustic Tomography of Thick Biological Tissues Toward Breast Imaging", *Technology in Cancer Research & Treatment*, vol. 4- 5, pp. 559-565, 2005.
Kuo et al., "Photoacoustic Imaging of Prostate Brachytherapy Seeds in Ex Vivo Prostate", in *SPIE Medical Imaging*, Lake Buena Vista, Florida, 2011, pp. 796409-01-796409-07.
Kuo et al., "Real-time Photoacoustic Imaging of Prostate Brachytherapy Seeds Using a Clinical Ultrasound System", Journal of Biomedical Optics, vol. 17-6, pp. 066005-1 to 066005-10, Jun. 2012.
Kwan et al., "Effect of Advanced Imaging Technology on How Biopsies Are Done and Who Does Them", *Radiology*, vol. 256-3, Sep. 2010.
Machi et al., "Ultrasound-Guided Radiofrequency Thermal Ablation of Liver Tumors: Percutaneous, Laparoscopic, and Open Surgical Approaches", *Journal of Gastrointestinal Surgery*, vol. 5-5, pp. 477-489, Oct. 2001.
Maurer et al., "The Accuracy of Image Guided Neurosurgery Using Implantable Fiducial Markers", in *Computer Assisted Radiology*, Berlin, 1995, pp. 1197-1202.
Menack et al., "Staging of pancreatic and ampullary cancers for resectability using laparoscopy with laparoscopic ultrasound.", *Surg Endosc*, vol. 15-10, pp. 1129-1134, Oct. 2001.
Myronenko et al., "Point-Set Registration: Coherent Point Drift", *IEEE Trans. on Pattern Analysis and Machine Intelligence*, vol. 32-12, pp. 2262-2275, 2010.
Okazawa et al., "Methods for segmenting curved needles in ultrasound images", Medical Image Analysis, vol. 10-, pp. 330-342, 2006.
Olgin et al., "Electrophysiological Effects of Long, Linear Atrial Lesions Placed Under Intracardiac Ultrasound Guidance", Circulation, vol. 96-, pp. 2715-2721, 1997.
Poon et al., Comparison of calibration methods for spatial tracking of a 3-D ultrasound probe. Ultrasound in Medicine and Biology 31(8), 1095-1108, Aug. 2005.
Reed et al., "Intraoperative Fluoroscopic Dose Assessment in Prostate Brachytherapy Patients", International Journal of Radiation Oncology, Biology, Physics, vol. 63-1, pp. 301-307, 2005.
Rivaz et al., "Real-Time Regularized Ultrasound Elastography.", IEEE Trans. Med. Imaging, vol. 30-4, pp. 928-945, 2011.
Rivaz et al., "Ultrasound Elastography: A Dynamic Programming Approach", IEEE Transactions on Medical Imaging, vol. 27-10, pp. 1373-1377, Oct. 2008.
Rohling et al., "PUPIL: Programmable Ultrasound Platform and Interface Library", in Medical Image Computing and Computer Assisted Interventions, 2003. pp. 424-431.
Stefansic et al., "Registration of Physical Space to Laparoscopic image space for use in minimally invasive hepatic surgery", IEEE Trans Med Imaging, vol. 19-10, pp. 1012-1023, Oct. 2000.
Stoll et al., "Passive Markers for Ultrasound Tracking of Surgical Instruments", in Medical Image Computing and Computer-Assisted Interventions, 2005. pp. 41-48.
Su et al., "Photoacoustic imaging of clinical metal needles in tissue", JBiomed Opt., vol. 15-2, pp. 021309.1-6, 2010.
Su et al., "Photoacoustic imaging of coronary artery stents", Optics Express, vol. 17-22, pp. 19894-19901, 2009.
Su et al., "Photoacoustic imaging of prostate brachytherapy seeds", Biomedical Optics Express, vol. 2-8, pp. 2243-2254, 2011.
Treeby et al., k-Wave: MATLAB toolbox for the simulation and reconstruction of photoacoustic wave-fields. *Journal of Biomedical Optics* 15(2), 021314 (2010).
Tsai et al., "A Versatile Camera Calibration Technique for High-Accuracy 3D Machine Vision Metrology Using Off-the-Shelf TV Cameras and Lenses", IEEE Journal of Robotics and Automation, vol. RA-3-4, pp. 323-358, 1987.
Tsai et al., "Near-infrared absorption property of biological soft tissue constituents", *J Med. Biol. Eng.*, vol. 21-, pp. 7-14, 2001.
Ukimura et al., "Imaging-Assisted Endoscopic Surgery: Cleveland Clinic Experience",*Journal of Endourology*, vol. 22-4, p. in press, Apr. 2008.
Ukimura et al., "Real-Time Transrectal Ultrasound Guidance During Laparoscopic Radical Prostatectomy: Impact on Surgical Margins", *The Journal of Urology*, vol. 175-4, pp. 1304-1310, 2006.
Valluru et al., "Photoacoustic Imaging: Opening New Frontiers in Medical Imaging", *Journal of Clinical Imaging Science*, vol. 1-2, pp. 1-7, 2011.
Vledder et al., "Intra-operative ultrasound elasticity imaging for monitoring of hepatic tumour thermal ablation", HPB (Oxford), vol. 12-10, pp. 717-723, Dec. 2010.
Vyas et al., Interoperative Ultrasound to Stereocamera Registration using Interventional Photoacoustic Imaging. in Medical Imaging 2012: Visualization, Image-Guided Procedures, and Modeling, San Diego, Feb. 4-9, 8316, 83160S (2012).
Wang et al., The developing market for medical robotics, Proceedings of the IEEE 94(9), 1763-1771, Sep. 2006.
Wein et al., "Automatic Registration and Fusion of Ultrasound with CT for Radiotherapy", in *Medical Image Computing and Computer Assisted Intervention*, 2005, pp. 303-311.
Wexner et al., "The current status of robotic pelvic surgery: results of a multinational interdisciplinary consensus conference", *Surgical Endoscopy*, vol. 23-, pp. 438-443, 2009.
Wiles et al., Accuracy assessment and interpretation for optical tracking systems. Proceedings of SPIE, 5367, 421-432 (2004).
Xu et al., Photoacoustic imaging in biomedicine. Review of scientific instruments 77, 041101 (2006).
Yao et al., "Photoacoustic tomography: fundamentals, advances and prospects", Contrast Media Mol. Imaging, vol. 6-, pp. 332-345, 2011.
Yip, T. K. Adebar, R. N. Rohling, S. E. Salcudean, and C. Y. Nguan, "3D Ultrasound to Stereoscopic Camera Registration through an Air-Tissue Boundary", in Medical Image Computing and Computer-Assisted Interventions (MICCAI), Beijing, Sep. 20-24, 2010. pp. 626-634.
Berber et al., "Resection versus Laparoscopic Radiofrequency Thermal Ablation of Solitary Colorectal Liver Metastasis", *Journal of Gastrointestinal Surgery*, vol. 12-11, pp. 1967-1972, Nov. 2008.
Besl et al., "A Method for Registration of 3-D Shapes", *IEEE Transactions on Pattern Analysis and Machine Intelligence*, vol. 14-2, pp. 239-256, 1992.
Esenaliev et al, (1999). Sensitivity of laser opto-acoustic imaging in detection of small deeply embedded tumors. IEEE Journal on Selected Topics in Quantum Electronics, 5(4), 981-988.
International Search Report issued in PCT Application No. PCT/US2013/030273 dated Jul. 25, 2013.

(56) References Cited

OTHER PUBLICATIONS

Lee et al (2011). A medical augmented-reality system for image-guided surgery using marker-added ICP. International Journal of Innovative Computing, Information and Control, 7(11), 6523-6539.
Leven et al., "DaVinci Canvas: A Telerobotic Surgical System with Integrated, Robot-Assisted, Laparoscopic Ultrasound Capability", in Medical Image Computing and Computer-Assisted Interventions, Palm Springs, CA, 2005. pp. 811-818. PMID: 16685945.
Maintz, J. et al "A survey of medical image registration," Medical image analysis 2(1), 1-36 (1998).
Navab et al., Camera-Augmented Mobile C-Arm (CAMC) Application: 3D Reconstruction using Low Cost Mobile C-Arm. in MICCAI 1999, 688-697 (1999).
Oberheide, U., et al, (2003). Optoacoustic imaging for optimization of laser cyclophotocoagulation. Journal of Biomedical Optics, 8(2), 281-287.
Pilatou, M. C., et al. (2003). Photoacoustic monitoring of changes in the blood circulation. Review of Scientific Instruments, 74(1 II), 384-386.
Rivaz et al., "Ablation Monitoring with Elastography: 2D In-vivoand 3D Ex-vivoStudies", in Med Image Comput Comput Assist Intery (MICCAI), New York, Sep. 6-10, 2008. pp. 458-466.
Rivaz et al., "Tracked Regularized Ultrasound Elastography for Targeting Breast Radiotherapy", in Med Image Comput Comput Assist Interv. ( MICCAI), London, Sep. 20-24, 2009. pp. 507-515.
Stolka et al., "A 3D-elastography-guided system for laparoscopic partial nephrectomies", in Medical Imaging 2010: Visualization, Image-Guided Procedures, and Modeling, San Diego, Feb. 13-18, 2010. pp. 762511-762511-12.
ten Brinke, G. A., et al (2008). Photoacoustic 3D visualization of tumor angiogenesis. Paper presented at the Progress in Biomedical Optics and Imaging—Proceedings of SPIE, , 6920.
Vagvolgyi et al., "The Surgical Assistant Workstation", in 2008 MICCAI Workshop—Systems and Architectures for Computer Assisted Interventions, New York, Sep. 6, 2008, p. in electronic proceedings at http://midasjournal.org/browse/publication/295.
Vagvolgyi et al., "Video to CT Registration for Image Overlay on Solid Organs", in 4th Workshop on Aubmented Environments for Medical Imaging and Computer-Aided Surgery, Sep. 10, 2008.
Xia et al (2008). An integrated system for planning, navigation and robotic assistance for skull base surgery. International Journal of Medical Robotics and Computer Assisted Surgery, 4(4), 321-330.
Bell M.A.L., et al., "In Vivo Visualization of Prostate Brachytherapy Seeds With Photoacoustic Imaging," Journal of Biomedical Optics, Dec. 2014, vol. 19(12), p. 126011.
Chan C., et al., "A Needle Tracking Device for Ultrasound Guided Percutaneous Procedures,"Ultrasound in medicine & biology, 2005, vol. 31 (11), pp. 1469-1483.
Cheng A., et al., Concurrent Photoacoustic Markers for Direct three-dimensional Ultrasound to Video Registration, Proc. SPIE BiOS, 2014, 89435J-89435J-9.
Cheng A., et al.., "Direct 3D Ultrasound to Video Registration Using Photoacoustic Markers," Journal of Biomedical Optics , 2013, vol. 18(6), 10 pages.
Choti, "Radiofrequency Ablation," Cancer Journal, 2000, vol. 6-4, pp. S291-S292.
Fischler M.A., et al., "Random Sample Consensus: A Paradigm for Model Fitting With Applications to Image Analysis and Automated Cartography," Communications of the ACM, 1981, vol. 24(6), pp. 381-395.
Fleming I.N., et al., "Ultrasound Elastography: Enabling Technology for Image Guided Laparoscopic Prostatectomy," in SPIE Medical Imaging 2009: Visualization, Image-guided Procedures and Modeling., Orlando, Florida, Jan. 2009, pp. 7261-7273, 10.1117/12.806507.
Frazier C.H., et al. , "Synthetic Aperture Techniques with a Virtual Source Element," Ultrasonics, Ferroelectrics, and Frequency Control, IEEE Transactions on, 1998, vol. 45(1), pp. 196-207.

Harrison T., et al., "The Applicability of Ultrasound Dynamic Receive Beamformers to Photoacoustic Imaging," IEEE Transactions on Ultrasonics, Ferroelectrics, and Frequency Control, 2011, vol. 58(10), pp. 2259-2263.
Jensen J.A., et al., "Calculation of Pressure Fields From Arbitrarily Shaped, Apodized, and Excited Ultrasound Transducers," IEEE Transactions on Ultrasonics, Ferroelectrics, and Frequency Control, Mar. 1992, vol. 39(2), pp. 262-267.
Kang H.J., et al., "Software framework of Real-time photoacoustic imaging system for Prostate Brachytherapy Seeds," Journal of Biomedical Optics, Feb. 2012, in SPIE Medical Imaging, San Diego, 2 pages.
Khosravi.S., et al., "One-step Needle Pose Estimation for Ultrasound Guided Biopsies," Conference Proceedings . IEEE Engineering in Medicine and Biology Society, 2007, pp. 3343-3346.
Kolkman R.G.M., et al., "Real-time in Vivo Photoacoustic and Ultrasound Imaging," Journal of Biomedical Optics , 2008, vol. 13(5), p. 050510.
Kortbek J., et al., "Synthetic Aperture Sequential Beamforming,"Proc. in IEEE International Ultrasonics Symposium, 2008, pp. 966-969.
Li M.L., et al., "Improved in Vivo Photoacoustic Microscopy Based on a Virtual-detector Concept,"Optics Letters, 2006, vol. 31, pp. 474-476.
Liao C.K., et al., "Optoacoustic Imaging with Synthetic Aperture Focusing and Cohehrence Weighting,"Optics Letters, 2004, vol. 29, pp. 2506-2508.
Niederhauser J.J., et al., "Comparision of Laser-induced and Classical Ultrasound," Proceedings of SPIE, 2003, vol. 4960, pp. 118-123.
Nikolov S., et al., "Virtual Ultrasound Sources in High Resolution Ultrasound Imaging," Proceedings of SPIE, Progress in biomedical optics and imaging, 2002, vol. 3, pp. 395-405.
Park S., et al., "Adaptive Beamforming for Photoacoustic Imaging Using Linear Array Transducer,"in IEEE Ultrasonics Symposium Proceedings , 2008, pp. 1088-1091.
Prager R.W., et al., "Decompression and Speckle Detection for Ultrasound Images Using the Homodyned K-distribution,"Pattern Recognition Letters , 2003, vol. 24(4), pp. 705-713.
Seabra J., et al., "Modeling Log-Compressed Ultrasound Images for Radio Frequency Signal Recovery," 30th Annual International Conference of the IEEE, Engineering in Medicine and Biology Society (EMBS 2008), 2008, 4 pages.
Simonetti F., "A Guided Wave Technique for Needle Biopsy Under Ultrasound Guidance," Proceedings of Spie , 2009 , vol. 7261 , pp. 726118.
Üstüner K.F., et al., "Ultrasound Imaging System Performance Assessment," presented at the 2003 American Association of Physicists in Medicine Annu. Meeting, San Diego, CA, 2003, 32 pages.
Thomenius K.E., "Evolution of Ultrasound Beamformers," Proceedings of IEEE Ultrasonics Symposium, 1996, vol. 2, pp. 1615-1622.
Tsunoi Y., et al., "Compact Acoustic-resolution Photoacoustic Imaging System with Fiber-based Illumination," Jpn. Journal of Applied Physics, 2014, vol. 53(12), p. 126701.
Written Opinion for International Application No. PCT/US2013/030273, dated Jul. 25, 2013, 4 pages.
Yin B., et al., "Fast Photoacoustic Imaging System Based on 320-element Linear Transducer Array," Phys. Med. Bioi., 2004, vol. 49(7), pp. 1339-1346.
Zemp R.J .,et al., "Photoacoustic Imaging of the Microvasculature With a High-frequency Ultrasound Array Transducer," Journal of Biomedical Optics , 2007 , vol. 12(1) , pp. 010501.
Zhang H.K., et al., "Coded Excitation Using Periodic and Unipolar M-sequences for Photoacoustic Imaging and Flow Measurement," Optics Express, 2016, vol. 24(1), pp. 17-29.
Zhang H.K., et al., "Photoacoustic Reconstruction Using Beamformed RF Data: A Synthetic Aperture Imaging Approach," In Proceedings of SPIE, 2015, vol. 9419, 94190L, 7 pages.
Hossbach, M., et al., "Simplified Stereo-Optical Ultrasound Plane Calibration", SPIE, Ultrasonic Imaging, Tomography, and Therapy, 2013, vol. 86750, pp. 86750X.

(56) References Cited

OTHER PUBLICATIONS

Piras, D., et al., "Photoacoustic Needle: Minimally Invasive Guidance to Biopsy", Journal of Biomedical Optics, Jul. 2013, vol. 18 (7), pp. 070502-1-070502-3.
Wei, C., et al., "Real-Time Integrated Photoacoustic and Ultrasound (PAUS) Imaging System to Guide Interventional Procedures: Ex Vivo Study," IEEE Transactions on Ultrasonics, Ferroelectrics, and Frequency Control, Feb. 2015, vol. 62 (2), pp. 319-328.
Zamanizadeh, E., et al., "Wavefront Segmentation and Classification for Model-Based Underwater High-Frequency Tomography", Oceans, 2012, 10 pages.
Cheung C.C.P., et al., "Multi-Channel Pre-Beamformed Data Acquisition System for Research on Advanced Ultrasound Imaging Methods", IEEE Transactions on Ultrasonics, Ferroelectrics, and Frequency Control, Feb. 2012, vol. 59 (2), pp. 243-252.
Mari J.M., et al., "Acquire Real-time RF Digital Ultrasound Data from a Commercial Scanner", Electronic Journal «Technical Acoustics», 2007, vol. 3, pp. 1-16.

* cited by examiner

PHOTOACOUSTIC TRACKING AND REGISTRATION IN INTERVENTIONAL ULTRASOUND

CROSS-REFERENCE OF RELATED APPLICATION

This is a national stage application under 35 U.S.C. § 371 of PCT/US2013/030273 filed Mar. 11, 2013, the entire contents of which are incorporated herein by reference and this application claims priority to U.S. Provisional Application No. 61/608,910, filed Mar. 9, 2012, the entire contents of which are hereby incorporated by reference.

This invention was made with government support under grant numbers EB015638 awarded by the National Institutes of Health and 1162095 awarded by the National Science Foundation. The government has certain rights in the invention.

BACKGROUND

1. Field of Invention

The field of the currently claimed embodiments of this invention relates to intraoperative registration and tracking systems, and more particularly to intraoperative registration and tracking systems that use photoacoustic tracking and registration in interventional ultrasound.

2. Discussion of Related Art

Intraoperative ultrasound (IOUS) imaging can be extremely useful in surgery and other interventional procedures. Ultrasound (US) systems provide real time 2D and 3D views into the patient's anatomy with relatively unobtrusive hardware and without the use of ionizing radiation. An increasing variety of transcutaneous, laparoscopic, and catheter-based probes including both 2D and 3D arrays are available from multiple vendors; image quality is rapidly improving; and advanced image processing techniques are increasing the variety of information that can be provided to the surgeon. Consequently, there is increasing interest in using IOUS in both open and laparoscopic surgery [8-10], in providing guidance for biopsies [11], tumor ablation therapy [12, 13], brachytherapy [14], and recently robotic surgery [15, 16].

One significant factor limiting the use of IOUS is the necessity for the surgeon to relate the information in the ultrasound images to preoperative information such as CT or MRI images and to what he or she is seeing in a laparoscopic video monitor or in direct viewing. Computer-based information fusion and imaging systems have significant potential to overcome this limitation, but they should address three main challenges to be useful in minimally invasive surgery. First, reliably and accurately registering intraoperative ultrasound to the surgical scene as observed by endoscopic video cameras. Second, it can also be important to accurately register and fuse pre-operative models continuously to the surgical scene. This feature can be especially important when IOUS cannot provide the needed information to guide the intervention. Third, after guiding the intervention tool using IOUS data and/or pre-operative models, there is often a need to identify a tool in the ultrasound images and to recover its position relative to patient anatomy. This requirement can be crucial in ablative therapy treatment, biopsy and needle steering scenarios, where the tool may be especially difficult to see and accurate placement on anatomic targets is required.

There are important limitations with the conventional approaches. Typically, systems for integrating IOUS for information support or intraoperative guidance use an electromagnetic or optical navigational tracker to provide real-time information about the position of the ultrasound probe relative to the patient, endoscopic cameras, and other equipment in the surgical environment (e.g., [17-23]). However, these approaches have serious limitations. Navigational trackers typically track sensors or markers relative to a separate base station placed somewhere close to the surgical environment, thus adding complexity. Optical systems require that the markers be visible to the optical sensors or cameras in the base. Electromagnetic systems require wires between the sensors and base unit, thus complicating sterility, are subject to field distortions, and may not work well in the presence of metal. Accuracy in estimating tool tip position is limited by tool shaft bending and the effects of angle estimation error if markers are placed at a distance from the tip, and it is often impractical to embed sensors near the tips of small tools such as needles or the tines of ablation probes. In addition, the estimation of IOUS-to-camera or IOUS-to-tool transformations necessarily requires an indirect calculation based on multiple tracking targets and is subject to error buildup. Furthermore, calibration of US imaging probes to tracking devices is tedious. Therefore, there remains a need for improved intraoperative registration and tracking systems.

SUMMARY

An intraoperative registration and tracking system according to some embodiments of the current invention includes an optical source configured to illuminate tissue intraoperatively with electromagnetic radiation at a substantially localized spot so as to provide a photoacoustic source at the substantially localize spot, an optical imaging system configured to form an optical image of at least a portion of the tissue and to detect and determine a position of the substantially localized spot in the optical image, an ultrasound imaging system configured to form an ultrasound image of at least a portion of the tissue and to detect and determine a position of the substantially localized spot in the ultrasound image, and a registration system configured to determine a coordinate transformation that registers the optical image with the ultrasound image based at least partially on a correspondence of the spot in the optical image with the spot in the ultrasound image.

BRIEF DESCRIPTION OF THE DRAWINGS

Further objectives and advantages will become apparent from a consideration of the description, drawings, and examples.

FIG. 9A) flood illumination; FIG. 9B) local illumination from fibers in tool.

DETAILED DESCRIPTION

Figure 1:
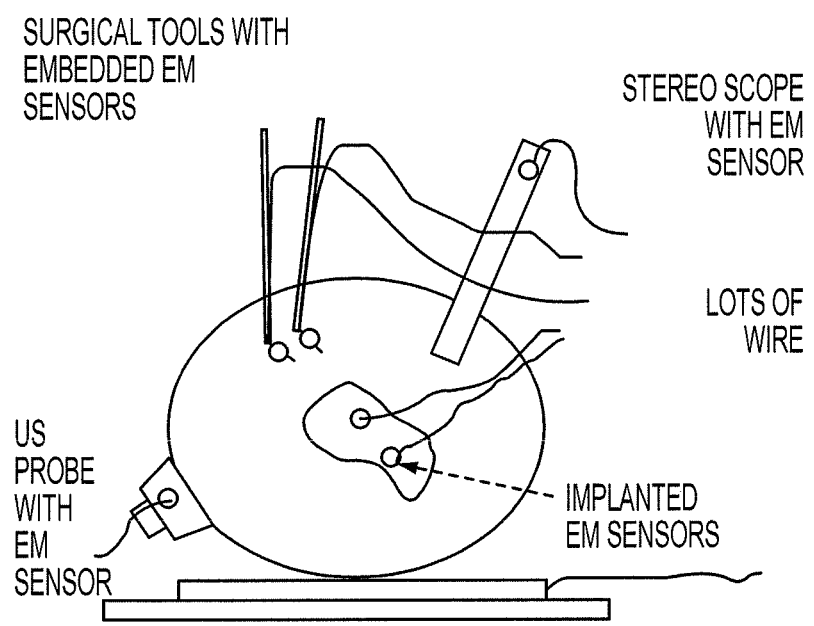
FIG. 1 is a schematic illustration of a typical EM-based laparoscopic IOUS guidance and visualization system [3].

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

The terms "light" and "optical" are intended to have a broad meaning. They can include, but are not limited to, the visible regions of the electromagnetic spectrum. They can include nonvisible regions of the electromagnetic spectrum such as infrared and ultraviolet light, and even x-ray and microwave regions. As long as the electromagnetic radiation can deposit a localized spot of energy that generates ultrasound, and the spot can be detected along with a corresponding image, it can be included in some embodiments.

The term "photoacoustic" is intended to have a broad definition which can be photons at any energy suitable for the particular application that deposit energy that generates an acoustic signal in a body of interest. This is intended to be sufficiently broad to include photons of microwave energy. The term "thermoacoustic" effect is often used with reference to microwave energies. The term photoacoustic as used herein is intended to include thermoacoustic in the broad definition.

The term "body" refers general to a mass, and not specifically to a human or animal body. In some applications, the body of interest can be a human or animal organ, or a portion thereof.

The term "spot" is intended to have a broad meaning. It can be point-like or a small circular or oval shape. However, it can also can be a pattern, such as, but not limited to an x shape, a v shape, a Z shape, and N shape, etc.

The term "substantially localized spot" means a spot of a size and of defined boundaries sufficient for the particular application. (In the case of a pattern, the localization can be with respect to one sub-feature of the pattern.) For example, most surgeries may require spots sizes from 0.5 to 2 mm. However, some surgeries may require more precision than other surgeries and the imaging geometries may vary. Consequently, the general concepts of the current invention are not limited to particular sizes and location precision of the spots.

The term "interstitial" means to be inserted into tissue, such as, but not limited to, a needle inserted into tissue with the inserted tip being surrounded by the tissue.

The term "real-time" is intended to mean that the images can be provided to the user during use of the system. In other words, any noticeable time delay between detection and image display to a user is sufficiently short for the particular application at hand. In some cases, the time delay can be so short as to be unnoticeable by a user.

We use "3DPA" to mean 3D photoacoustic images and "3DUS" to mean conventional 3D ultrasound images or the overall system. The same transducer can be used for both and both have the same coordinate system, and we can use "3DUS coordinates" and "3DPA coordinates" interchangeably.

Intraoperative ultrasound (IOUS) imaging is being used increasingly as a guidance modality in interventional procedures—including open and laparoscopic surgery [8, 24], local ablations [13, 25-27], brachytherapy [14], intracardiac procedures [28, 29], etc. Using IOUS images requires that the surgeon relate these images to the physical reality of the patient's anatomy and the motions of surgical tools. Similarly, IOUS images are increasingly "fused" or registered to preoperative data such as CT or MRI images or surgical planning (e.g., [17, 30]), and the results are used to help guide an intervention. Again, the surgeon must relate the registered images to the physical coordinate system associated with the patient's anatomy and other interventional tools. Although this process was traditionally performed in the surgeon's head, surgical navigation and guidance systems are becoming more prevalent and have become "standard of care" in some areas. Typically, these systems rely on a combination of navigational tracking of surgical instruments, "registration" of preoperative and intraoperative data, and some form of information displaying to make the information available to the surgeon. Robotic systems such as the DaVinci surgical robot [31] typically relate the motions of tools to a "visualization" coordinate system associated with a video endoscope and provide means for displaying other images, but rely on the surgeon to relate this data to the video images.

Real time registration of ultrasound images and preoperative data to intraoperative video display has been a significant challenge. This could become increasingly important as advanced ultrasound imaging methods are increasingly developed and deployed in minimally invasive surgery (MIS). For example, in recent work, we have demonstrated the use of ultrasound elastography (USE) for monitoring ablation of liver tumors [22, 32], image-guided prostatectomies [33], and breast cancer radiotherapy targeting [34], and as a "bridge" for co-registering preoperative CT with intraoperative video in laparoscopic partial nephrectomy (LPN) [3]. Generally, the conventional approaches (e.g., [35-37]) have been to place tracking devices on IOUS probes, the endoscope, and surgical instruments. However, this indirect approach is subject to error buildup from multiple tracking and calibration errors, thus limiting the accuracy of the IOUS to intraoperative image registration.

Because they have no line-of-sight restrictions, electromagnetic (EM) systems are the most commonly used tracking systems for laparoscopic surgery, flexible endoscopy, and other MIS applications. In these environments EM sensors may be attached to tools, IOUS probes, and cameras, and may be implanted into moving or deforming organs for use as fiducial landmarks (FIG. 1). For example, in prior work targeting laparoscopic partial nephrectomies (LPN), we have used EM tracked US probes to obtain 3D US/USE images of lesions in kidneys [3]. These images have been registered with preoperative CT and used to create a real time video overlay display of the tumor within the kidney, which was tracked using a small EM sensor implanted into the tumor, thus providing continuing feedback on intact tumor location and resection margins during resection.

However, EM sensors have a number of drawbacks that make them less than ideal for use in laparoscopic surgery, especially if a robot is involved. In addition to the obvious problems associated with field distortion from close proximity of the robot, EM systems have problems that apply more broadly to any laparoscopic or MIS environment. These include: intrusive integration of a large EM "base station" and other equipment into the surgical field; field distortion from other metallic objects or during electrocautery and ablation treatment; interference between tools working in close proximity to each other; dealing with EM sensor wire leads; increased cost in sterilizing tools with associated sensors; and overall cost-effectiveness, especially when we include the needed pre-operative calibration and preparation time to ultrasound probes, cameras and the tools.

Optical tracking systems such as [38, 39] avoid the field distortion problems associated with EM devices and may be slightly more accurate, but line of sight restrictions often make them impractical for use inside the body, and placing them outside the body can result in degraded tracking accuracy for long or flexible tools or laparoscopic imaging probes, even if the various tracking targets are all visible to the tracker.

Accurate tracking of surgical tools and devices in ultrasound images is very difficult, due to several factors including image quality, tool size, orientation and depth, and limitations of current tracking technologies, although there has been some work to address these issues. One straightforward approach (e.g., [18]) embeds small EM sensors into needles, catheters, and other tools. Others seek to find tools directly from IOUS images. For example, Stoll et al. [40] have attached a set of passive markers by which the position and orientation of a surgical instrument can be computed from its ultrasound image. The identification of these passive markers, however, still relies on the quality of ultrasound images and the type of the surrounding tissues. Similarly, Rohling et al. have applied extensive image processing methods to detect needle shafts [41] and also have investigated a beam forming approach to steer the beam to maximize the tool visibility [42]. All of these approaches need to have an optimal orientation (i.e. needle in US plane) and considerable size for the tool to be identified and recovered accurately.

Some embodiments of the current invention use photoacoustic (PA) imaging to overcome many of these limitations [1, 2, 4, 43, 44]. PA imaging [45, 46] is based on the photoacoustic effect, originally discovered by Alexander Graham Bell. In PA imaging, an object is usually irradiated by a short-pulsed, non-ionizing laser beam. Some of the delivered energy is absorbed, according to optical absorption properties of the target tissue or other material, and converted into heat, leading to transient thermoelastic expansion and thus wideband ultrasonic emission, which can be detected by conventional IOUS probes and processed to produce high contrast images. Since the effect is sensitive to tissue density, composition and properties such as hemoglobin oxygen saturation, it is useful both for anatomic and functional imaging. There is current interest in using PA to locate small objects such as needles or brachytherapy seeds within the body [5, 43, 44, 47, 48]. Some embodiments of the current invention are directed to such systems. For example, we have shown repeatable average registration accuracy of 0.56±0.28 mm in artificial phantoms [1] and 0.42±0.15 mm in ex vivo liver [1], 0.38±0.27 mm for Kidney and 0.85±0.45 mm for fat, compared to ~1.7-3 mm for artificial phantoms and ~3-5 mm for tissue obtained with other methods (e.g., [3, 7, 49, 50]).

Some embodiments of the current invention use PA methods to replace navigational trackers in ultrasound-guided surgery and other minimally invasive interventions, together with the systems and techniques for doing this. Some embodiments use PA imaging to perform real-time registration between the ultrasound and video image spaces. This approach does not require a base station and does not require implanted fiducial markers to complete the video-to-ultrasound registration needed for providing "augmented reality" guidance and information support in endoscopic surgery. Further, since the image-to-image registration is more direct than tracker-based methods, it can be less likely to be affected by extraneous errors and can provide significant accuracy advantages [1].

In some embodiments, small implanted PA fiducial markers can also be used to track tissue and organ motion after an initial registration. This can eliminate any dependence on implanted EM fiducials for tracking. This also can provide other advantages such as simplicity, directness, and accuracy in some embodiments. We also note that the PA markers may themselves be used as registration fiducials in cases where they may have been implanted for preoperative imaging. Clinical investigators often perform tumor biopsy before operation. Small FDA approved particles can be injected to facilitate several follow up treatment steps including precise repeated biopsy, post-operative imaging and accurate guidance during surgery. Small particles within the resection margin need to be resected with the tumor and hence another use of PA imaging is to detect these markers after resection to assure negative margins.

Three projected PA spots is sufficient for registration to stereo cameras, since the 3D locations of the PA spots relative to the cameras may be found by triangulation and the 3D locations relative to ultrasound come directly from localization in 3DUS. Registration to monoscopic cameras, such as conventional endoscopes, may be accomplished by the use of more points. For example, the well-known method of Bopp and Krauss (H. Bopp and H. Krauss, "An Orientation and Calibration Method for Non-Topographic Applications", Photogrammetric Engineering and Remote Sensing, vol. 44-9, pp. 1191-1196, September, 1978) may be used if five or more spots are available. However, many other methods known in the art may also be used instead. Another example is the method of Tsai (R. Y. Tsai, "A Versatile Camera Calibration Technique for High-Accuracy 3D Machine Vision Metrology Using Off-the-Shelf TV Cameras and Lenses", IEEE Journal of Robotics and Automation, vol. RA-3-4, pp. 323-358, 1987.).

Some embodiments of the current invention can include a safety system. In some embodiments, laser light is delivered through optical fibers into the patient's body for laparoscopic surgery. It is desirable to ensure that no laser light escapes from the patient's body, or at least below a safe threshold. In an embodiment, additional light can be added to the optical path, such as the optical fiber. The optical fiber can be a multimode optical fiber, for example, to be able to transmit a plurality of beams of light at relatively spaced wavelengths. (However, this does not preclude the use of single mode optical fibers, other types of waveguides, and/or free space illumination, depending on the particular application.) For example, a low energy infrared light source from an LED or laser may be used as sort of a guide channel, or safety signal. Detectors placed outside the body can detect this monitoring light even in cases when the higher power laser used to create the PA effect is turned off. Safety circuits or other safety monitoring devices can prevent the higher power laser from being turned on if the monitoring light is detected and/or a suitable warning signal such as an audible alarm can be triggered. The monitoring light may be modulated at a known frequency, or with other suitable modulation, and matched to suitable detection circuits to increase sensitivity. The use of infrared light is suitable for some applications because its presence will not distract the surgeon. However, visible or other wavelengths of light can be used is other embodiments of the current invention. A similar system may also be deployed within the laser system enclosure itself to ensure that stray laser light does not escape from the enclosure.

Figure 2:
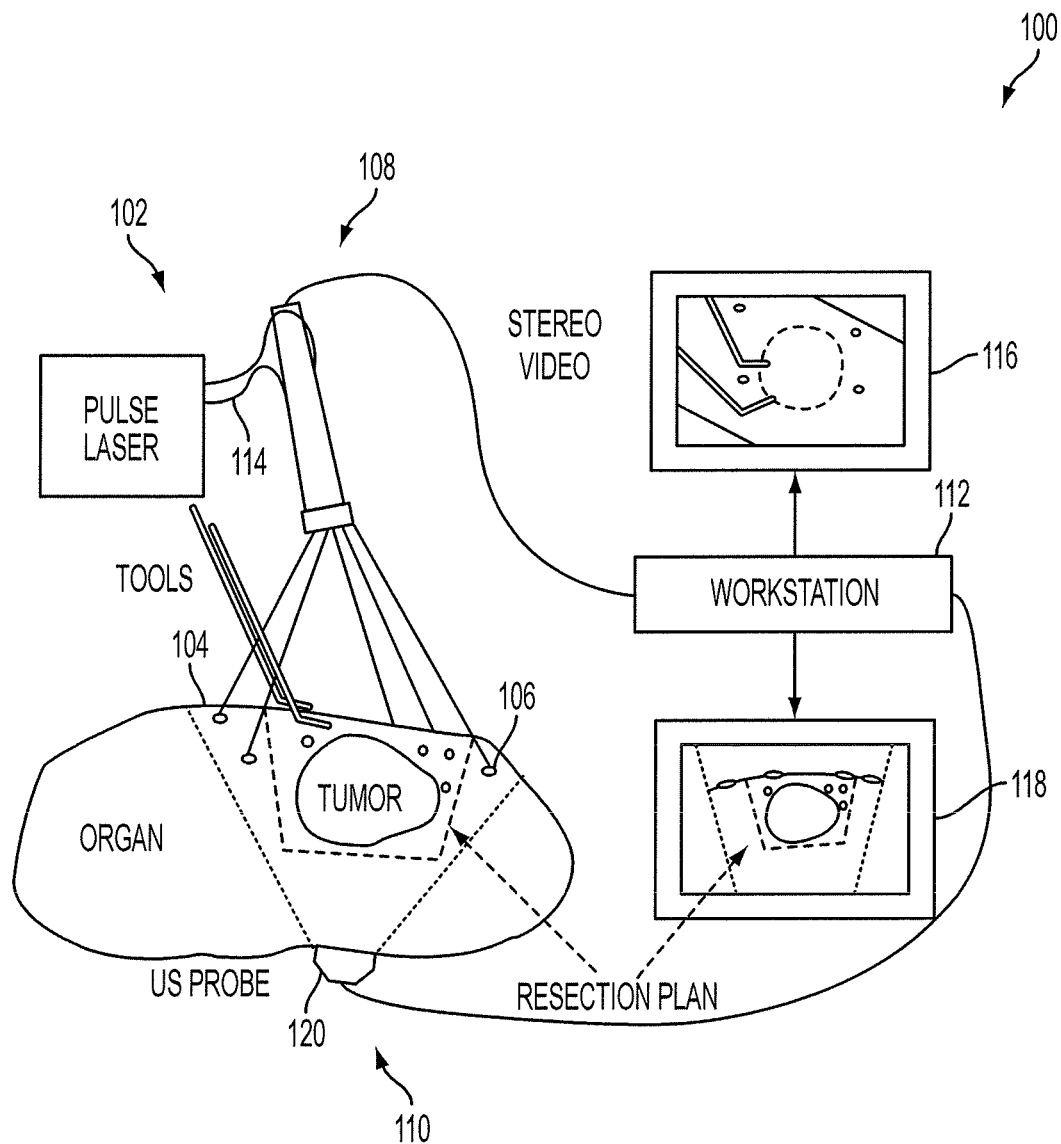
FIG. 2 is a schematic illustration of an intraoperative registration and tracking system according to an embodiment of the current invention.

FIG. 2 provides a schematic illustration of an intraoperative registration and tracking system 100 according to an embodiment of the current invention. The intraoperative registration and tracking system 100 includes an optical source 102 configured to illuminate tissue 104 intraoperatively with electromagnetic radiation at a substantially localized spot (e.g., 106) so as to provide a photoacoustic source at the substantially localize spot, and an optical imaging system 108 configured to form an optical image of at least a portion of the tissue 104 and to detect and determine a position of the substantially localized spot (e.g., corresponding to 106) in the optical image. The intraoperative registration and tracking system 100 also includes an ultrasound imaging system 110 configured to form an ultrasound image of at least a portion of the tissue 104 and to detect and determine a position of the substantially localized spot (e.g., corresponding to 106) in the ultrasound image; and a registration system 112 configured to determine a coordinate transformation that registers the optical image with the ultrasound image based at least partially on a correspondence of the spot in the optical image with the spot in the ultrasound image.

The optical source 102 can be configured to provide pulsed radiation and/or continuous wave radiation in some embodiments. The pulsed radiation can be provided by a pulsed laser, as is illustrated in the example of FIG. 2. In some embodiments, the optical source 102 can include one or more pulsed lasers. However, the general concepts of the current invention are not limited to only the use of lasers. In some embodiments, a pulsed laser that is selectively frequency double can be used. This can permit the selective use of two different illuminating wavelengths. Some embodiments can use two or more pulsed laser, each of which could be selectively frequency double. In some embodiments, the optical source 102 can include a tunable pulsed laser to permit greater flexibility in selecting illumination wavelengths. The pulsed radiation can be electromagnetic radiation at any suitable wavelength for the particular application. In many applications, pulsed radiation within the visible, infrared and/or ultraviolet wavelength ranges is suitable. However, the broad concepts of the current invention are not limited to pulsed sources only in these ranges. As long as the radiation provides photons that can be absorbed to provide an acoustic response with a sufficiently small focus for the application, it could be used in some embodiments.

The optical source 102 can include additional LEDS and/or lasers in some embodiments. For example one or more continuous wave (cw) laser can be included to provide illumination for the optical imaging system 108 to form images of the tissue. The cw laser, or lasers, can be within the visible, infrared and/or ultraviolet wavelength ranges. In some embodiments, the optical source 102 can also have a source of light for a leakage detection system. This can be a dual use of one of the cw lasers for both illuminating for imaging and light leakage detection, or a separate source. In some embodiments, an infrared laser is suitable for leakage detection.

The optical source 102 can further include an optical fiber 114. Although one optical fiber is illustrated in FIG. 2, two, three or more optical fibers can be used. The optical source 102 can include optical components to selectively couple light from the one or more lasers into the same optical fiber and/or to selectable optical fibers from a plurality of optical fibers. In some embodiments, the optical fiber 114, and any additional optical fibers, can be a multimode optical fiber to be able to transmit different wavelengths of light either sequentially, or concurrently. In other words, multiplexing different wavelengths at the same time can be provided, but is not required in all embodiments. However, the general concepts of the current invention do not preclude the use of single mode optical fibers in some embodiments. In the embodiment of FIG. 2, the optical fiber 114 is attached to a structure containing pick-up elements of a video system. This can be, but is not limited to, an endoscope, for example. Alternatively, the optical fiber 114 could be attached to a surgical tool, for example. In some embodiments, there can be a plurality of optical fibers with one or groups attached to different objects, such as, but not limited to, a plurality of surgical tools including an endoscope. In some embodiments, the optical source 102 can illuminate the tissue at two or more spots, either in sequence, or at the same time. Optical components can be included in the optical source 102 to scan the illumination beam according to some embodiments, such as, but not limited to a scanning mirror arrangement.

The registration system 112 is configured to determine a coordinate transformation that registers the optical image with the ultrasound image based at least partially on a correspondence of the spot in the optical image with the spot in the ultrasound image. In general, the images and coordinate transformations can be of any dimensions. For example, they can be one-dimensional, two-dimensional and/or three-dimensional images and coordinate transformations.

The registration system 112, as well as some or all of the signal processing for the optical imaging system 108 and ultrasound imaging system, can be implemented on a work station as is illustrated in FIG. 2. These components can be implemented through software by programming the workstation, for example. However, in other embodiments, one or more of these components could be implemented on dedicated hardware, such as, but not limited to, ASICs and/or FPGAs. In addition, the workstation can have one or more CPUs and/or GPUs. Preoperative data can also be registered with the optical and ultrasound images in some embodiments. This can be implemented on workstation 112 through software, or could be implemented through dedicated hardware. A tracking system to track surgical tools and other objects can also be implemented on workstation 112, either through software, or hardware. In some embodiments, the registering of optical images, ultrasound images and/or preoperative images and/or tracking of objects can be done in real time during an operation.

The intraoperative registration and tracking system 100 can include one or more displays 116, 118, according to an embodiment of the current invention. The displays 116 and/or 118 can be display screens as illustrated in FIG. 2, or any other suitable display. For example, in embodiments in which the intraoperative registration and tracking system 100 is integrated into a robotic system, the displays can be the stereo console displays.

The ultrasound imaging system 110 includes an ultrasound probe 120 to at least operate as an ultrasound receiver to receive signals from the PA sources. In some embodiments, the ultrasound probe 120 may operate as both an ultrasound receiver to receive signals from the PA sources, and as a transmitter and receiver to supplement ultrasound images obtained by the PA sources. In general, the ultrasound imaging system 110 can be an imaging system of any dimension. For example, it can be a one-dimensional, two-dimensional and/or three-dimensional ultrasound imaging system. In the case of a one-dimensional system, it may be viewed as a system that provides range information along a line.

Figure 3:
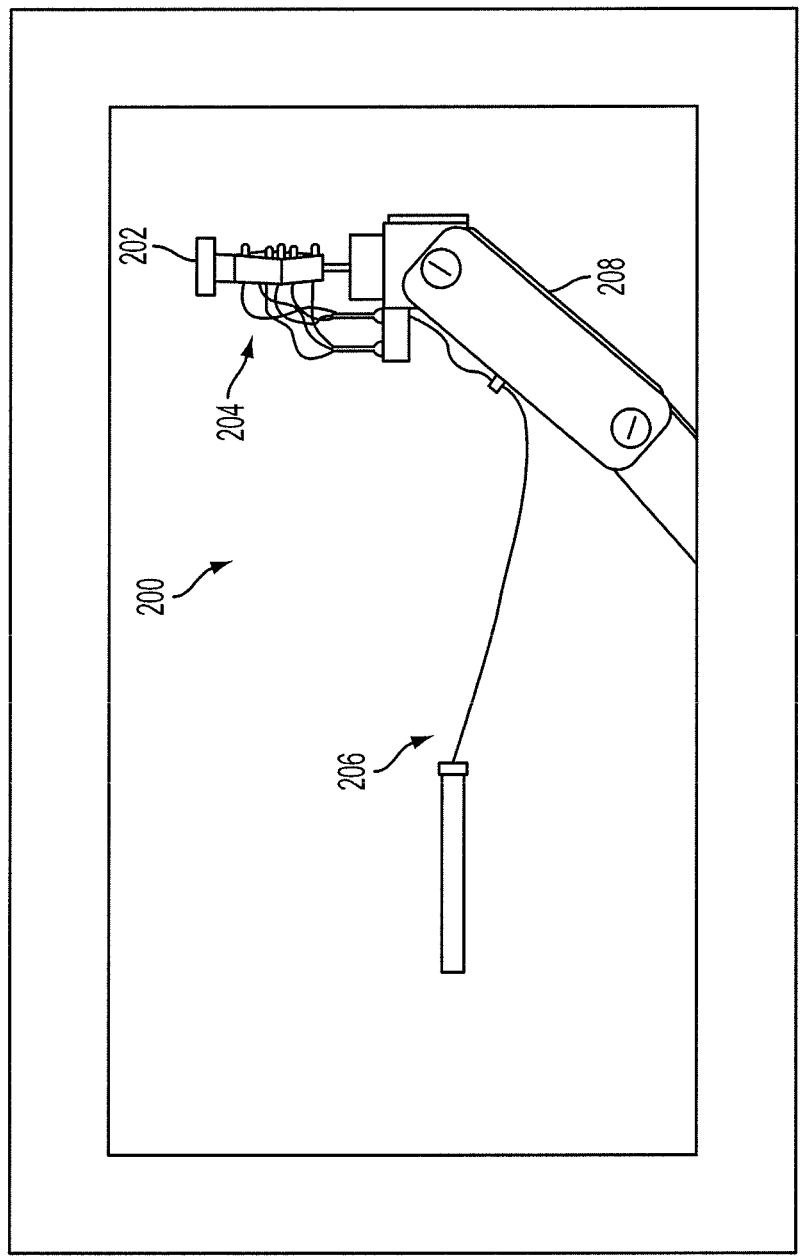
FIGS. 3-5 are schematic illustrations of portions of an intraoperative registration and tracking system according to another embodiment of the current invention.
Figure 4:
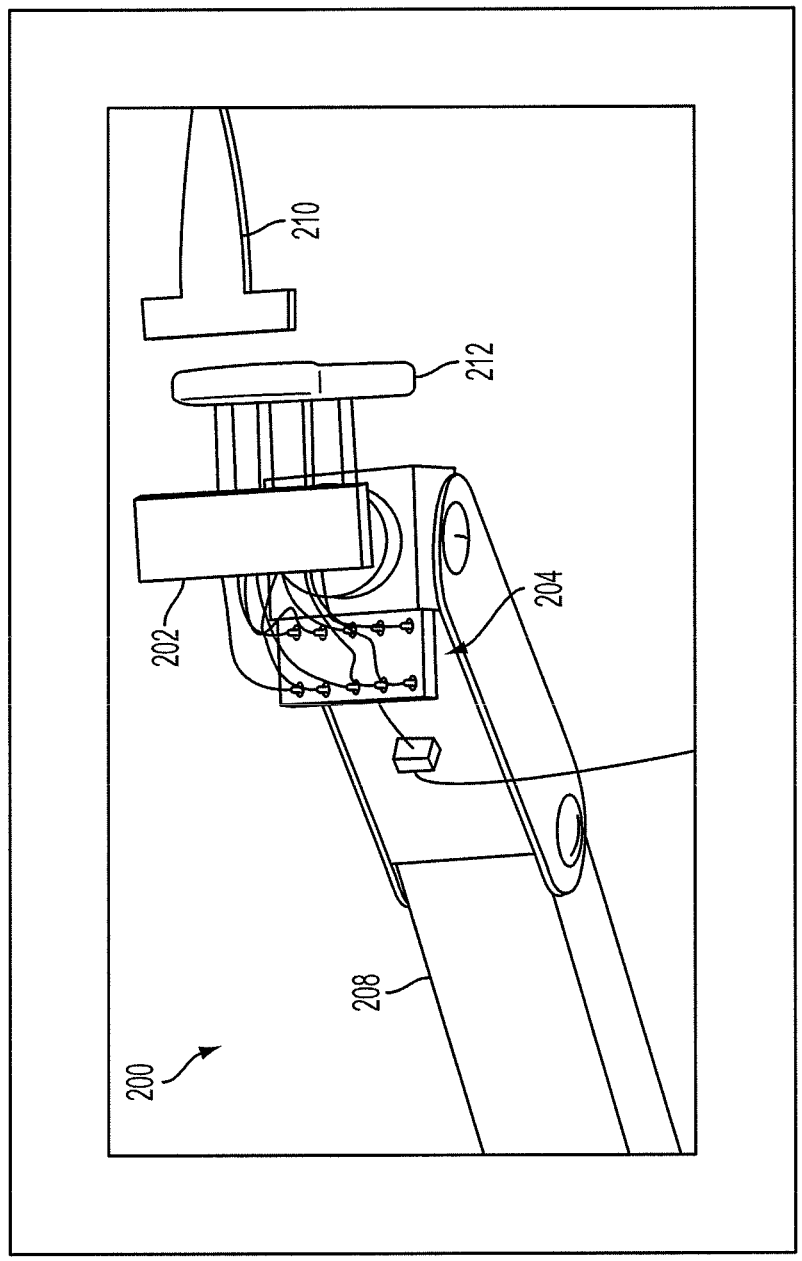
Figure 5:
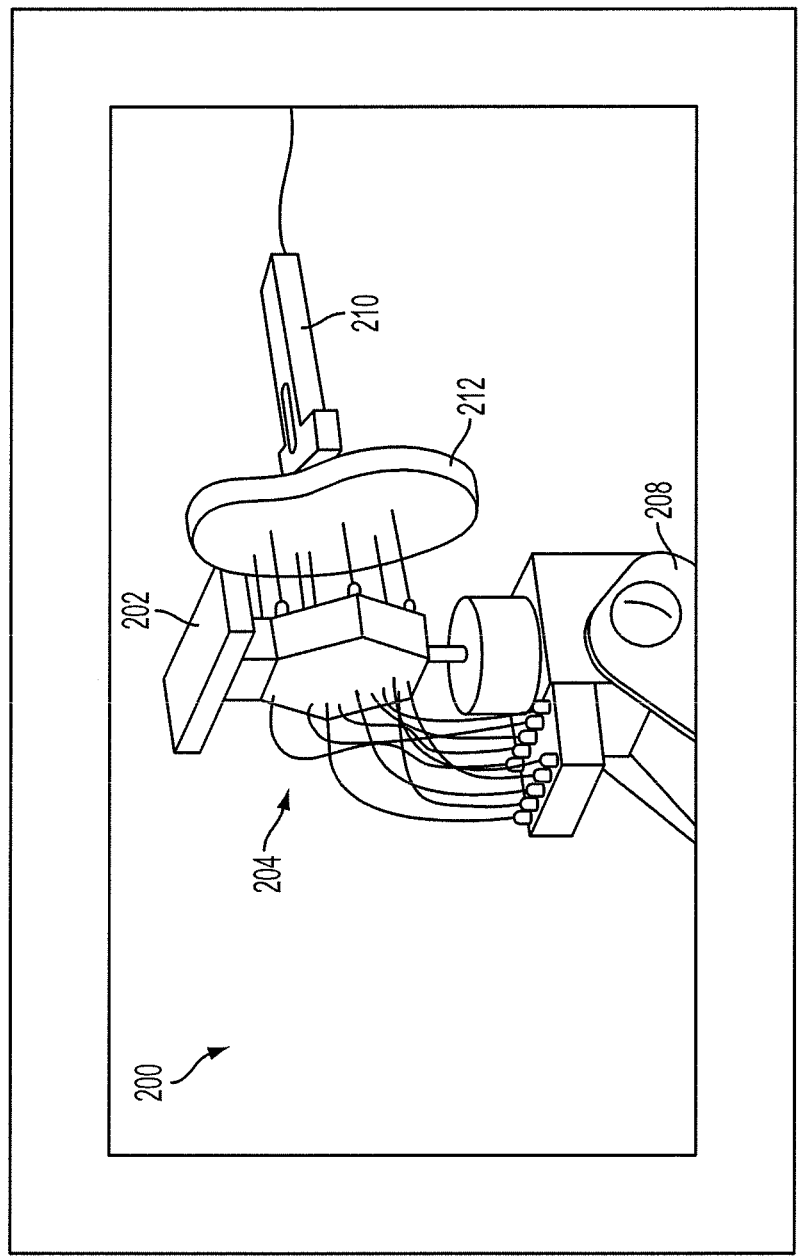

FIGS. 3-5 provide a schematic illustration of a portion of an intraoperative registration and tracking system 200 according to another embodiment of the current invention. In this embodiment, a stereo camera 202 and a plurality of optical fibers 204 for the optical source 206 are attached to a turret 108. The turret can be part of a robotic system, or a stand-alone system. It can also be configured for use in open surgery, for example. FIGS. 4 and 5 also show the ultrasound probe 210 and the tissue 212.

The following examples will describe some more details of some embodiments of the current invention. However, the broad concepts of the current invention are not limited only to these particular examples.

Example 1

Although the interventional PA techniques according to some embodiments of the current invention are can be broadly applicable, in the current example, we use laparoscopic partial nephrectomies (LPN) and RF ablation of tumors in solid organs such as the liver and kidney. For the LPN application a typical workflow would be as follows: Preoperative CT would be used to plan the surgical resection. Intraoperatively, the surgeon would position the kidney so that the tumor is close to the surface facing the surgeon and a 3DUS probe would be placed on the opposite side of the kidney in a position where the tumor, surrounding tissue, and organ surface is visible in the ultrasound. PA-to-video registration would be performed continuously using a system according to an embodiment of the current invention. 3DUS-to-CT registration would be performed and overlay images would be generated on ultrasound and video images, showing the segmented tumor and resection plan. Using this information, the surgeon may use electrocautery to mark the borders of the resection region. Using combined US and video overlay guidance, the surgeon will place several small fiducial markers within the planned resection volume, and another CT/IOUS registration will be done. The markers can be located and tracked with PA imaging concurrently with PA-video registration. The tracked markers can be used to maintain registration to the registered preoperative information and to generate visualization overlays to assist the surgeon in performing the resection. We note that many variations on this workflow are possible. For example, if preoperative CT is not available, PA-to-video registration may still be used to generate overlay images for guidance, so long as the fiducials and organ surface remain visible to the US probe. After resection, PA imaging may be used to detect any markers left behind, thus indicating possible inadequate margins. Similarly, if preoperative biopsy is performed, then the surgeon may choose to leave behind markers that may be used for intraoperative targeting and tracking. A workflow for resection of liver tumors would be similar.

For RF ablation of tumors, PA-to-video registration may be used to enable image overlays to assist in placing the ablation probe. The targeted tumors may be located either in 3DUS or through 3DUS-to-CT registration. In the latter case, small implanted fiducials may be used to assist in real time tracking of tumor targets. Photoacoustic imaging would be used to permit the surgeon to accurately visualize the small tines of the ablation probe relative to the chosen ablation target sites.

System Overview:

In this example, the system (FIG. 2) includes 1) a laser illumination system; 2) a 3D ultrasound (3DUS) system; and 3) a video camera system, all interfaced to a PC/GPU workstation. Depending on the application, either stereo or monoscopic video may be used. For the current example, we use both stereo and monoscopic conventional camera setups available in our lab. Alternatively, we could also use conventional laparoscopes and the stereo endoscope from the DaVinci robot system in our mock operating room lab, for example. However, the general concepts of the current invention are not limited to these examples. The illumination system can direct a pattern of high-energy laser pulses along with co-located lower energy visible continuous wave (CW) laser light onto the surface of an organ within the field of view of the video system. The illumination system may be mounted with the camera, as shown in the figure, or may be placed independently, so long as it shines spots where they are visible from the camera. Energy absorbed from the pulsed laser spots will generate PA signals that may be imaged by the ultrasound system, thus creating a pattern of "virtual" surface fiducial markers. Since the co-located CW beams are visible at all times in the video camera, the registration between video and ultrasound coordinate systems can be performed. Since the ultrasound images can concurrently locate implanted fiducials or other structures within the target organ, registration and tracking of preoperative images or other data relative to the video coordinate system may likewise be accomplished. Similarly, surgical tools or catheters can be illuminated to generate PA signals that may be used to locate them relative to ultrasound images and, hence, to the video coordinate system as well.

Figure 6:
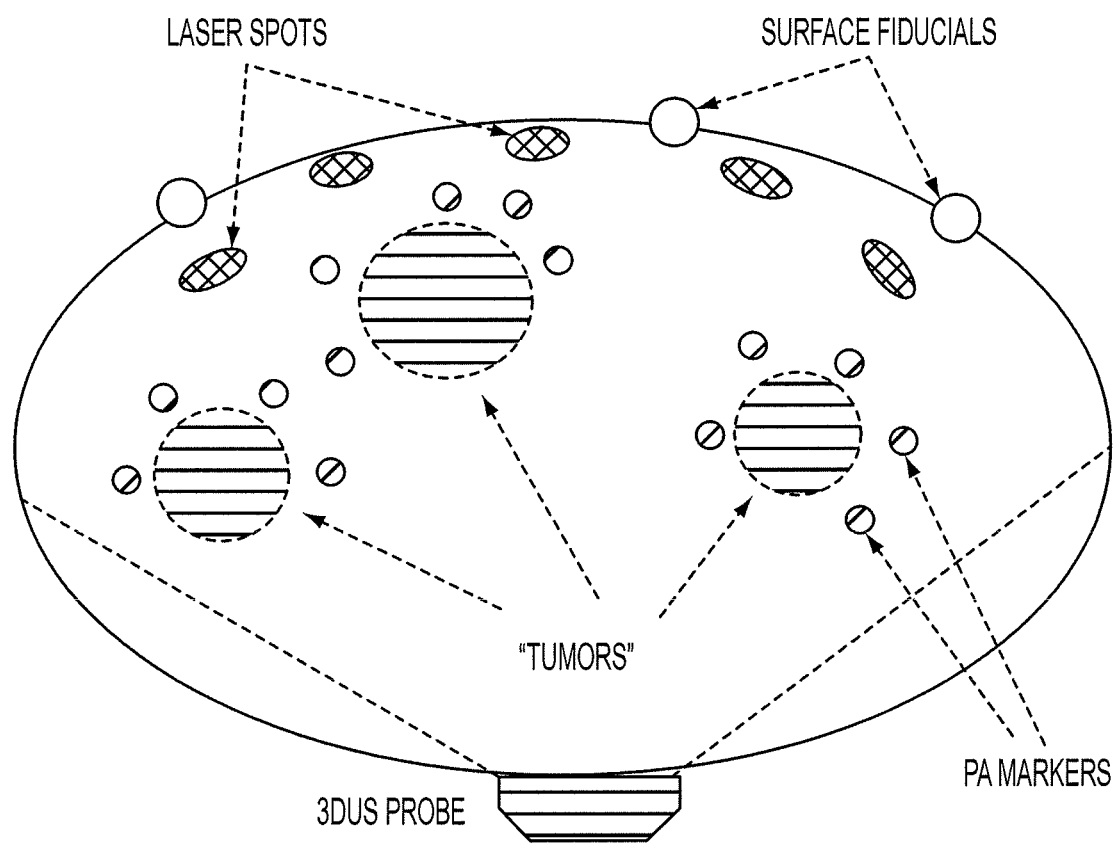
FIG. 6 is a schematic illustration of a phantom design to test some embodiments of the current invention.

Phantoms:

For these examples, we will adapt previous work [3] to create an artificial kidney phantom shown schematically in FIG. 6. The phantom body can be composed of PLASTI-SOL™ (MF Manufacturing Co., Inc., Fort Worth, Tex.) with ultrasonic scatterer materials. Into this, we can implant gel-based fiducial spheres simulating tumors with diameters ranging from 5 mm to 10 mm, doped to be readily visible in CT, x-ray, and conventional 3DUS images. Small, brightly colored plastic spheres can be embedded on the surface of the phantom so as to be easily located in 3DUS and video images. Small photoacoustic marker objects can also be embedded in the phantom near the tumors. To compare the contrast of PA signals in a realistic model, we can produce similar phantoms in which ex vivo pig kidneys. The livers are substituted for the PLASTISOL body material and suitably doped alginate is injected to provide the implanted tumors [52]. Additionally, we can also introduce a small tube (INTRAMEDIC™, BD, Franklin Lakes, N.J.) filled with animal blood, placed near to the surface and near to the PA markers to verify different aspect of this embodiment of the current invention. These phantoms can be CT scanned to provide an accurate "ground truth" for validation experiments.

For accurate, real-time registration of video to 3D ultrasound coordinate systems, there are three principal components, as discussed below.

Laser Illumination System:

In this example, a fiber-based light delivery system can be used, as illustrated schematically in FIG. 2. To facilitate localization of the laser spots in video images, the pulsed laser light can be combined with low power continuous wave (CW) light from a separate source and transmitted via optical fiber to a beam splitter using standard optics techniques. Our current Q-switched laser source has two main wavelength outputs: 1064 nm and the frequency doubled 532 nm output. The 532 nm laser light is green in color and can produce a strong photoacoustic signal since it is strongly absorbed by the soft tissues and blood [53, 54], typical of most surgeries [47, 53]. The 1064 nm light has greater penetration depth than the 532 nm light. This is mainly because both Hb and $HbO_2$ have less optical absorption coefficient at 1064 nm compared to 532 nm [47, 53, 54]. For surface laser spots, we can investigate the use of both 532 nm and 1064 nm light. With our recent PA experiments utilizing kidney, liver [1] and fat, we have shown that 532 nm generates PA signals at the tissue-air interface. It is known that fat tissue has a relatively higher optical absorption coefficient at NIR range compared to 532 nm [55]. However, intraoperative fat is often covered with a thin layer of blood or other material that is highly responsive at 532 nm and since fat is not always present. However, we can also use alternate strategies, such as using 1064 nm or successive pulses of 532 and 1064 nm if fat is present. Alternatively, one can also make use of tunable wavelengths and low-cost pulsed laser diodes (PLD). Some data indicate that one can get usable PA surface images in phantoms with 2-16 µJ pulses, comparable to energy from available PLDs, according to some embodiments of the current invention.

Figure 7:
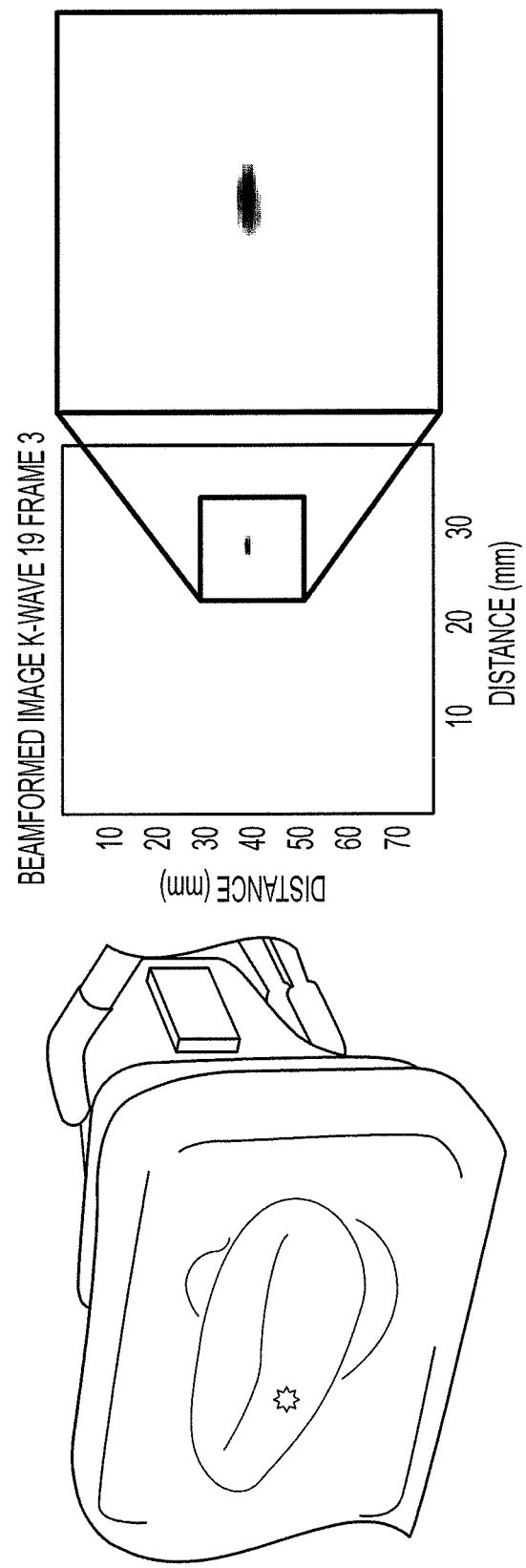
FIG. 7 shows tests of an example for an embodiment of the current invention: (left) Photograph of a scanned laser, US and stereo camera setup, in a typical trial. (middle, right) Photoacoustic image reconstructed from pseudo-spectra analysis and k-space Green's function method for one spot.

3DUS and Photoacoustic Imaging:

We can draw upon our extensive experience and systems infrastructure for interventional ultrasound research (see, e.g., our lab web sites [56, 57] and papers [1, 2, 4, 20, 22, 48, 49, 58, 59]). For this example, we have chosen to use 3D IOUS, both because it is increasingly used in interventional applications, and because some of the registration and tracking problems are more straightforward. We can use an existing Ultrasonix SonixRP (Ultrasonix, Vancouver, Calif.) system, for example, along with two mechanical 3D ultrasound probes: 1) a linear array with rotational actuation from Vernon Inc. (5-10 MHz), and 2) a linear array with precise translational actuation from NDK Inc. (5-10 MHz). We can also use a compact phased 3D array from NDK (5-10 MHz with 64*32 elements) that can permit rapid volume acquisition, for example. We have demonstrated our ability to form 3D PA images of laser spots projected onto the surface of a liver phantom (FIG. 7) [1, 2].

Video System and Video-US Registration:

We can work with both calibrated stereo and monoscopic camera setups and software libraries [60-63]. The bright spots projected onto the target surface can be located in video images and matched to corresponding bright spots in 3DPA images, whose positions relative to the 3DUS probe has been determined as described above. In the case of stereo video, standard methods can be used to determine the 3D positions of the points relative to camera coordinates, and standard 3D-3D registration methods (e.g., [64-67]) will be used to compute the transformation $F_{UC}$ between ultrasound and camera coordinates. For monoscopic cameras, standard 2D-3D photogrammetric methods (e.g., [68-70]) can be used. The achievable bandwidth for measuring $F_{UC}$ can be limited initially by the 10 Hz pulse rate permitted by our laser system and by the volume acquisition rate of our mechanically scanned 3DUS system probes, which can acquire 60 2D images per second. However, the laser pulses can easily be time-multiplexed to 20 and 40 Hz to provide a greater bandwidth. In alternative embodiments, one can make use of electronically scanned 2D array probes to provide 20-30 volumes per second.

Parameter Optimization:

We can evaluate our method on both artificial and ex vivo phantoms and in a small in vivo study. We can assess the accuracy of our registration by comparing the results IOUS to those obtained using the physical surface fiducials described earlier. We can locate these fiducials in conventional 3DUS images and in the same video images as for the laser spots. We can use the video-US registration methods to compute the US-to-camera transformations $F_{UC}^{PA}$ and $F_{UC}^{sfc}$ using the photoacoustic laser spots and conventional surface fiducials, respectively, along with the registration difference $DF_{UC}^{PA} = (F_{UC}^{PA})^{-1} F_{UC}^{sfc}$. The translational and rotational components $DF_{UC}^{PA}$ of may be represented by vectors $\overset{1}{e}$ and $\overset{1}{a}$, respectively, and (for small errors)

$$DF_{UC}^{PA} \overset{r}{v} \overset{r}{\approx} \overset{r}{a} \overset{r}{\times} \overset{r}{v} + \overset{r}{e}$$

for any $$\overset{1}{v}.$$

We can systematically vary the positions of the phantom, cameras, and ultrasound probe, compute $DF_{UC}^{PA}$ for each position, and perform statistical analysis on the corresponding 6 vectors $$\overset{1}{e}_k = [\overset{r}{e}_k, \overset{r}{e}_k]$$

in order to predict target registration error (TRE) [71, 72] statistics for points within the IOUS volume. We can also perform a leave-one-out analysis similar to [1] to estimate error statistics for points on the organ surface and can use these statistics to compute a separate estimate of volumetric TRE. We can repeat these procedures on our artificial phantom, on ex vivo phantoms with kidney, liver, and fat tissue, and on a limited in vivo study on two pigs. In these examples, we can systematically vary speed/resolution of the 3DUS probe; the intensity, wavelength, and aperture size of the laser pulses; and the imaging geometry in order to determine the optimal values and performance sensitivity of these parameters for system design. For the in vivo study, we can also determine the sensitivity to breathing artifacts. We can optimize parameters in the first pig and use these parameters in the second pig to estimate a 90% confidence "non-inferiority" bound d such that $m_V < m_E + d$ where $m_V$ and $m_E$ are the TREs for in vivo and ex vivo results.

Real-Time Tracking of Registered Preoperative Data

Intraoperative ultrasound has significant potential as a "bridge" between preoperative data such as surgical plans or CT and MRI images and intraoperative navigation and visualization systems. In this example, real-time, continuous tracking of registered preoperative models in 3DUS and video camera coordinates can be provided. Since the example above can provide accurate registration of 3DUS to video coordinates, the remaining barrier is finding a way to determine the 3DUS coordinates of targets that may not be directly visible in subsequent 3DUS images, once they have been determined by an initial registration step. As is often the case with tumors, we will assume that these targets and the immediately surrounding tissue are not highly deformable, so that their deformation may be modeled adequately by a rigid, affine, or similar low degree-of-freedom transformation.

Figure 8:
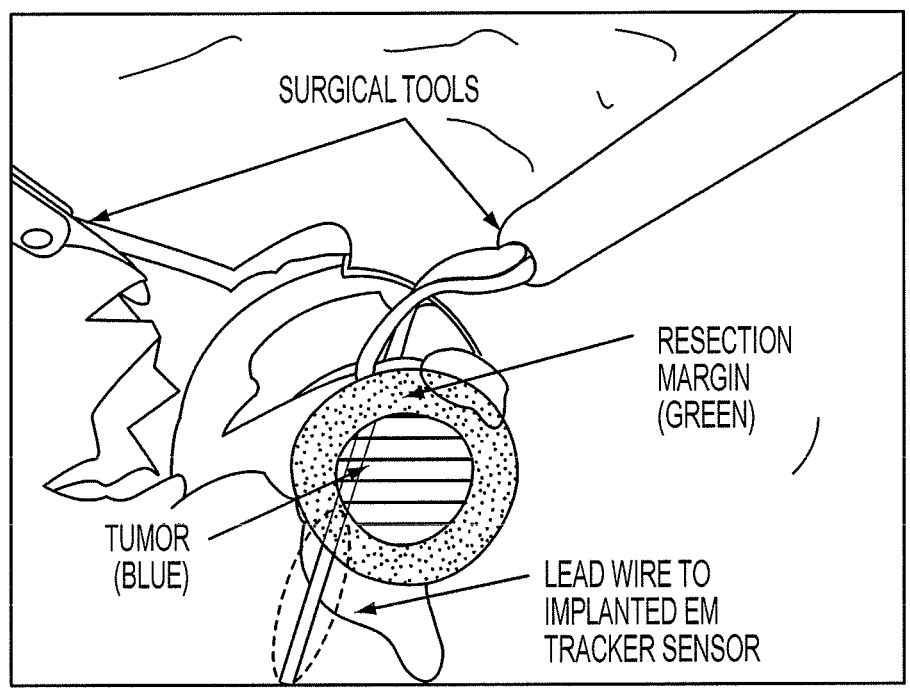
FIG. 8 shows an example of video overlay of preoperative model based on CT, registered from 3D IOUS, and tracked with EM [3] according to conventional approaches.

In prior work [3, 52], we demonstrated registration of ultrasound elastography and conventional IOUS images to preoperative CT images and resection plans for laparoscopic partial nephrectomies. One significant challenge for this application is maintaining registration of pertinent parts of the preoperative model in the presence of large anatomic changes during resection. Since the tumor and resection margin must remain intact, our approach in [3] was to implant small EM markers into or near the tumor and to track those to provide real time overlay for guiding the surgeon (FIG. 8). Although successful, this approach introduces complications in dealing with the wires, sterilization, calibration, unavoidable EM interference, and the size of the EM sensors.

According to an embodiment of the current invention, we replace the EM tracker sensors with small biocompatible metal fiducial objects that may be located readily in PA images (much more easily than in conventional US). These markers would be implanted in or near the target anatomy and localized in 3DPA images taken concurrently with the 3DUS images used for registration. For this tracking embodiment, we can use 1064 nm wavelength pulses, for example, to avoid high absorption by blood and tissue scattering and to achieve deep penetration into the target. We can use the phantom model to determine the point spread function of the PA system due to the impulse excitation, wide angle detection, and other system parameters. We can use standard Radon transform and back projection methods to reconstruct PA images and to determine the most effective system for this particular application. However, the broad concepts of the current invention are not limited to this example. In prior work [43, 44] we have demonstrated accurate, high-contrast PA imaging and localization of brachytherapy seeds in ex vivo dog prostate using 1064 nm laser pulses [4], and other groups have reported similar results (e.g., [5, 47, 73]). Based on our experience [4], we can construct 1 mm markers from the same brachytherapy material.

Figure 9A:
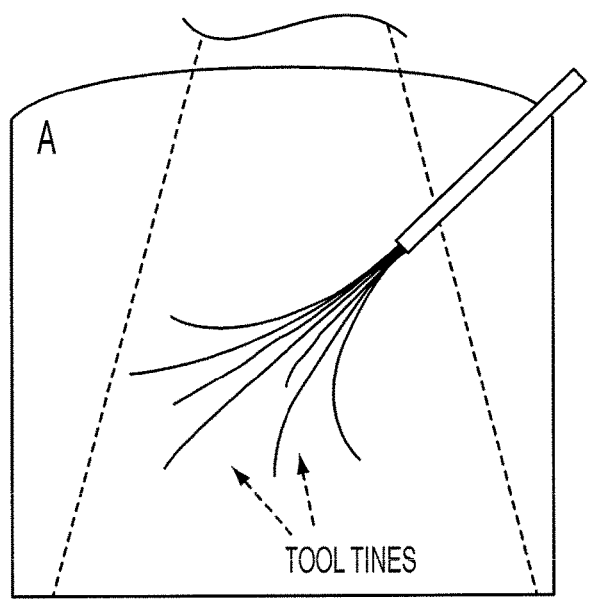
FIGS. 9A and 9B are schematic illustrations for identification of tines using PA approach according to two embodiments of the current invention.
Figure 9B:
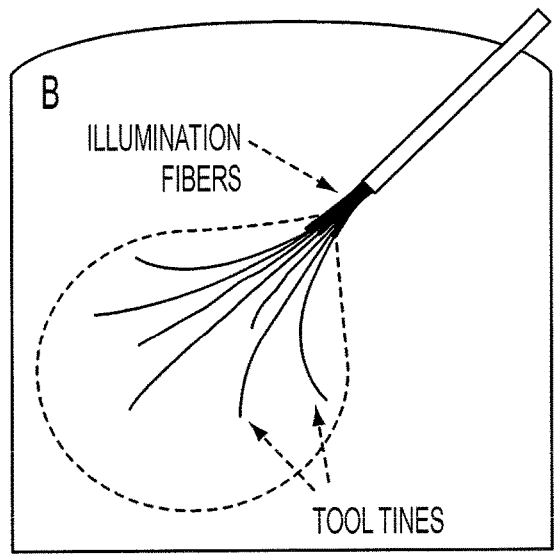

Once an initial registration is performed, the tracked positions of the markers can be used to continuously update the coordinate transformation between the preoperative model and 3DUS coordinates. The results from above can be used to enable graphic overlays on the video images similar to FIG. 9. For this example, we can implement rigid and simple affine transformations, but we note that higher order deformable transformations are also possible, depending on the application and number of markers.

As a test of an embodiment of the current invention, we can implant US-visible "tumors" and PA fiducials in phantoms and obtain initial 3DUS and 3DPA images. The 3DUS images can be segmented to produce models $M_i^0$ of the tumors relative to 3DUS coordinates. (Alternative: we can CT scan the phantom, segment to produce models at poses $F_i^{CT}$ in CT coordinates, register CT to 3DUS coordinates, and compute $M_i^0 = F_{UCT} M_i^{CT}$, where $F_{UCT}$ is the registration transformation). The positions $$\overset{1}{f}_{\ell,k}$$

of the PA fiducials near each tumor can be determined in 3DUS coordinates from the 3DPA images. We can then systematically modify the imaging arrangement by moving the 3DUS probe and/or distorting the phantom by cutting into it or stretching it and obtain new 3DUS and 3DPA images. The tumors can be re-segmented to produce models $M_i^{(t)}$. The positions $$\overset{1}{f}_{\ell,j}$$

of the PA fiducials can be determined and transformation parameters $$\overset{r(t)}{n}$$

computed such that $$\overset{1}{f}_{\ell,j} = T(\overset{1}{f}_{\ell,j}; \overset{r(t)}{n}).$$

We can then compare $M_k^{(t)}$ to $$T(M_k^0; \overset{r(t)}{n}),$$

using standard measures of 3D-3D registration accuracy, such as TREs, average surface distances, and DICE coefficients. We can perform the same procedure in vivo on pig kidneys and livers. In addition, we can create at least one phantom similar to that in FIG. 8, generate graphic overlays, and compare the overlay with the visible tumor.

REFERENCES

[1] A. Cheng, J. U. Kang, R. H. Taylor, and E. M. Boctor, "Direct 3D Ultrasound to Video Registration Using the Photoacoustic Effect", in Medical Image Computing and Computer-Assisted Intervention (MICCAI), Nice, October, 2012. p. (accepted).

[2] S. Vyas, S. Su, R. Kim, N. Kuo, R. Taylor, J. Kang, and E. Boctor, "Intraoperative Ultrasound to Stereocamera Registration using Interventional Photoacoustic Imaging", in SPIE Medical Imaging, San Diego, February, 2012.

[3] P. J. Stolka, M. Keil, G. Sakas, E. McVeigh, M. E. Allaf, R. H. Taylor, and E. M. Boctor, "A 3D-elastography-guided system for laparoscopic partial nephrectomies", in Medical Imaging 2010: Visualization, Image-Guided Procedures, and Modeling, San Diego, Feb. 13-18, 2010. pp. 76251I-76251I-12.

[4] N. Kuo, H. J. Kang, D. Y. Song, J. U. Kang, and E. M. Boctor, "Real-time Photoacoustic Imaging of Prostate Brachytherapy Seeds Using a Clinical Ultrasound System", Journal of Biomedical Optics, vol. 17-6, pp. 066005-1 to 066005-10, June, 2012.

[5] T. Harrison and R. J. Zemp, "Coregistered photoacoustic-ultrasound imaging applied to brachytherapy", J. Biomedical Optics, vol. 16-8, August, 2011.

[6] G. Ku, B. D. Fornage, X. Jin, M. Xu, K. K. Hunt, and L. V. Wang, "Thermoacoustic and Photoacoustic Tomography of Thick Biological Tissues Toward Breast Imaging", Technology in Cancer Research & Treatment, vol. 4-5, pp. 559-565, 2005.

[7] C. L. Cheung, C. Wedlake, J. Moore, S. E. Pautler, and T. M. Peters, "Fused Video and Ultrasound Images for Minimally Invasive Partial Nephrectomy: A Phantom Study", in Medical Image Computing and Computer-Assisted Interventions (MICCAI), Beijing, Sep. 20-24, 2010. pp. 408-415.

[8] O. Ukimura, C. Magi-Galluzzi, and I. S. Gill, "Real-Time Transrectal Ultrasound Guidance During Laparoscopic Radical Prostatectomy: Impact on Surgical Margins", The Journal of Urology, vol. 175-4, pp. 1304-1310, 2006.

[9] O. Ukimura and I. S. Gill, "Imaging-Assisted Endoscopic Surgery: Cleveland Clinic Experience", Journal of Endourology, vol. 22-4, p. in press, April, 2008.

[10] M. Menack, J. Spitz, and M. Arregui, "Staging of pancreatic and ampullary cancers for resectability using laparoscopy with laparoscopic ultrasound.", Surg Endosc, vol. 15-10, pp. 1129-34, October, 2001.

[11] S. W. Kwan, M. Bhargavan, and R. K. K. Jr., "Effect of Advanced Imaging Technology on How Biopsies Are Done and Who Does Them", Radiology, vol. 256-3, September 2010.

[12] M. Choti, "Surgical Management of Hepatocellular Carcinoma: Resection and Ablation", JVIR, vol. 33-9, pp. 871-6, 2002.

[13] M. Choti, M. E. Bohlman, and S. B. Solomon, "Robotically Assisted Radiofrequency Ablation of Liver Cancer", IHPBA, 2002.

[14] D. R. Reed, K. E. Wallner, S. Narayanan, S. G. Sutlief, E. C. Ford, and P. S. Cho, "Intraoperative Fluoroscopic Dose Assessment in Prostate Brachytherapy Patients", International Journal of Radiation Oncology, Biology, Physics, vol. 63-1, pp. 301-307, 2005.

[15] S. D. Wexner, R. Bergamaschi, A. Lacy, J. Udo, H. Brolmanm, R. H. Kennedy, and H. John, "The current status of robotic pelvic surgery: results of a multinational interdisciplinary consensus conference", Surgical Endoscopy, vol. 23-, pp. 438-443, 2009.

[16] S. Bhayani and N. Das, "Robotic assisted laparoscopic partial nephrectomy for suspected renal cell carcinoma: retrospective review of surgical outcomes of 35 cases", BMC Surgery, vol. 8-16, 2008.

[17] J. Stefansic, A. Herline, Y. Shyr, W. Chapman, J. Fitzpatrick, B. Dawant, and R. J. Galloway, "Registration of Physical Space to Laparoscopic image space for use in minimally invasive hepatic surgery", IEEE Trans Med Imaging, vol. 19-10, pp. 1012-1023, October, 2000.

[18] "SonixGPS—a revolutionary needle Guidance Positioning System," http://ultrasonix.com/products/gps, 2011.

[19] E. M. Boctor, Enabling Technologies For Ultrasound Imaging In Computer Assisted Intervention, thesis in Computer Science Department, Johns Hopkins University, 2006.

[20] E. M. Boctor, M. A. Choti, E. C. Burdette, and R. J. W. III, "Three-dimensional ultrasound-guided robotic needle placement: an experimental evaluation", Int. J of Medical Robotics and Computer Assisted Surgery, vol. 4-2, pp. 180-191, 2008.

[21] H. Rivaz, E. Boctor, P. Foroughi, R. Zellars, G. Fichtinger, and G. Hager, "Ultrasound Elastography: A Dynamic Programming Approach", IEEE Transactions on Medical Imaging, vol. 27-10, pp. 1373-1377, October, 2008.

[22] H. Rivaz, I. Fleming, L. Assumpcao, G. Fichtinger, U. M. Hamper, M. A. Choti, G. D. Hager, and E. Boctor, "Ablation Monitoring with Elastography: 2D In-vivo and 3D Ex-vivo Studies", in Med Image Comput Comput Assist Intery (MICCAI), New York, Sep. 6-10, 2008. pp. 458-466.

[23] P. Foroughi, H. Rivaz, I. Fleming, G. D. Hager, and E. M. Boctor, "Tracked Ultrasound Elastrography (TrUE)", Medical Image Computing and Computer Assisted Intervention, vol. 13-Pt 2, pp. 9-16, 2010.

[24] J. Machi, S. Uchida, K. Sumida, W. M. L. Limm, S. A. Hundahi, A. J. Oishi, N. L. Furumoto, and R. H. Oishi, "Ultrasound-Guided Radiofrequency Thermal Ablation of Liver Tumors: Percutaneous, Laparoscopic, and Open Surgical Approaches", Journal of Gastrointestinal Surgery, vol. 5-5, pp. 477-489, October 2001.

[25] M. Choti, "Radiofrequency Ablation", Cancer Jounal, vol. 6-4, pp. S291-2, 2000.

[26] M. A. Choti, "Surgical Management of Hepatocellular Carcinoma: Resection and Ablation", Journal of Vascular and Interventional Radiology, vol. 13-9 Pt 2, pp. S197-203, September 2002.

[27] E. Berber, M. Tsinberg, G. Tellioglu, C. H. Simpfendorfer, and A. E. Siperstein, "Resection versus Laparoscopic Radiofrequency Thermal Ablation of Solitary Colorectal Liver Metastasis", Journal of Gastrointestinal Surgery, vol. 12-11, pp. 1967-1972, November 2008.

[28] J. E. Olgin, J. M. Kalman, M. Chin, C. Stillson, M. Maguire, P. Ursel, and M. D. Lesh, "Electrophysiological Effects of Long, Linear Atrial Lesions Placed Under Intracardiac Ultrasound Guidance", Circulation, vol. 96-, pp. 2715-2721, 1997.

[29] J. W. Cannon, J. A. Stoll, I. S. Salgo, H. B. Knowles, R. D. Howe, P. E. Dupont, G. R. Marx, and P. J. d. Nido, "Real-Time Three-Dimensional Ultrasound for Guiding Surgical Tasks", Computer Aided Surgery, vol. 8-2, pp. 82-90, 2003.

[30] W. Wein, B. Roeper, and N. Navab, "Automatic Registration and Fusion of Ultrasound with CT for Radiotherapy", in Medical Image Computing and Computer Assisted Intervention, 2005, pp. 303-311

[31] G. S. Guthart and J. K. Salisbury, "The Intuitive Telesurgery System: Overview and Application", in Proc. of the IEEE International Conference on Robotics and Automation (ICRA2000), San Francisco, 2000, pp. 618-621

[32] H. Rivaz, E. Boctor, M. A. Choti, and G. D. Hager, "Real-Time Regularized Ultrasound Elastography.", *IEEE Trans. Med. Imaging*, vol. 30-4, pp. 928-945, 2011.

[33] I. N. Fleming, H. Rivaz, K. Macura, L.-M. Su, U. Hamper, T. Lotan, G. Lagoda, A. Burnett, Russell H. Taylor, G. D. Hager, and E. M. Boctor, "Ultrasound elastography: enabling technology for image guided laparoscopic prostatectomy", in SPIE Medical Imaging 2009: Visualization, Image-guided Procedures and Modeling, Orlando, Fla., January, 2009. pp. 7261-7273. 10.1117/12.806507

[34] H. Rivaz, P. Foroughi, I. Fleming, R. Zellars, E. Boctor, and G. Hager, "Tracked Regularized Ultrasound Elastography for Targeting Breast Radiotherapy", in Med Image Comput Comput Assist Interv. (MICCAI), London, Sep. 20-24, 2009. pp. 507-15.

[35] H. J. Kang, P. J. Stolka, and M. B. Emad, "OpenITGLinkMUSiiC: A Standard Communications Protocol for Advanced Ultrasound Research", *The MIDAS Journal*, 2011.

[36] R. S. J. Estépar, N. Stylopoulos, R. E. Ellis, E. Samset, C. Westin, C. Thompson, and K. Vosburgh, "Towards Scarless Surgery: An Endoscopic-Ultrasound Navigation System for Transgastric Access Procedures", in Medical Image Computing and Computer Assisted Intervention, 2006. pp. 445-453.

[37] R. S. J. Estépar, C. Westin, and K. G. Vosburgh, "Towards Real Time 2D to 3D Registration for Ultrasound-Guided Endoscopic and Laparoscopic Procedures", *International Journal of Computer Assisted Radiology and Surgery*, vol. 4-6, pp. 549-560, 2009.

[38] "Northern Digital *Polaris* Family of Optical Tracking Systems," http://www.ndigital.com/medical/polarisfamily.php, 2011.

[39] "Claron Technologies MicronTracker," http://clarontech.com/microntracker_technology.php,2011.

[40] J. Stoll and P. Dupont, "Passive Markers for Ultrasound Tracking of Surgical Instruments", in Medical Image Computing and Computer-Assisted Interventions, 2005. pp. 41-48.

[41] S. H. Okazawa, R. Ebrahimi, J. Chuang, R. N. Rohling, and S. E. Salcudean, "Methods for segmenting curved needles in ultrasound images", *Medical Image Analysis*, vol. 10-, pp. 330-342, 2006.

[42] R. Rohling, W. Fung, and P. Lajevardi, "PUPIL: Programmable Ultrasound Platform and Interface Library", in Medical Image Computing and Computer Assisted Interventions, 2003. pp. 424-431.

[43] E. Boctor, S. Verma, T. DeJournett, J. Kang, and J. Spicer, "Brachytherapy Seed Localization Using Combined Photoacoustic and Ultrasound Imaging (Abstract 7629-49)", in *SPIE Medical Imaging Conference* San Diego, 2010, p. 203

[44] N. Kuo, H. J. Kang, T. DeJournett, J. Spicer, and E. Boctor, "Photoacoustic Imaging of Prostate Brachytherapy Seeds in Ex Vivo Prostate", in *SPIE Medical Imaging*, Lake Buena Vista, Fla., 2011, pp. 796409-01-796409-07

[45] L. V. Wang and H. Wu, *Biomedical Optics: Principles and Imaging*: Wiley, 2007.

[46] "//en.wikipedia.org/wiki/Photoacoustic_imaging_in_biomedicine," http://en.wikipedia.org/wiki/Photoacoustic_imaging_in_biomedicine,

[47] J. L. Su, R. R. Bouchard, A. B. Karpiouk, J. D. Hazle, and S. Y. Emelianov, "Photoacoustic imaging of prostate brachytherapy seeds", *Biomedical Optics Express*, vol. 2-8, pp. 2243-54, 2011.

[48] H.-J. Kang, N. Kuo, and E. M. Boctor, "Software framework of Real-time photoacoustic imaging system for Prostate Brachytherapy Seeds", in SPIE Medical Imaging, San Diego, February, 2012.

[49] J. Leven, D. Burschka, R. Kumar, G. Zhang, S. Blumenkranz, X. Dai, M. Awad, G. Hager, M. Marohn, M. Choti, C. Hasser, and R. H. Taylor, "DaVinci Canvas: A Telerobotic Surgical System with Integrated, Robot-Assisted, Laparoscopic Ultrasound Capability", in Medical Image Computing and Computer-Assisted Interventions, Palm Springs, Calif., 2005. pp. 811-818. PMID: 16685945

[50] M. C. Yip, T. K. Adebar, R. N. Rohling, S. E. Salcudean, and C. Y. Nguan, "3D Ultrasound to Stereoscopic Camera Registration through an Air-Tissue Boundary", in Medical Image Computing and Computer-Assisted Interventions (MICCAI), Beijing, Sep. 20-24, 2010. pp. 626-634.

[51] J. Su, A. Karpiouk, B. Wang, and S. Emelianov, "Photoacoustic imaging of clinical metal needles in tissue", *J Biomed Opt.*, vol. 15-2, pp. 021309.1-6, 2010.

[52] M. Keil, P. J. Stolka, M. Wiebel, G. Sakas, E. R. McVeigh, R. H. Taylor, and E. Boctor, "Ultrasound and CT Registration Quality: Elastography vs. Classical B-Mode", in ISBI, 2009. pp. 967-970.

[53] S. Prahl, "Optical properties spectra compiled by Scott Prahl", http://omlc.ogi.edu/spectra/,

[54] C. Tsai, J. Chen, and W. Wang, "Near-infrared absorption property of biological soft tissue constituents", *J. Med. Biol. Eng.*, vol. 21-, pp. 7-14, 2001.

[55] J. Yao and L. V. Wang, "Photoacoustic tomography: fundamentals, advances and prospects", *Contrast Media Mol. Imaging*, vol. 6-, pp. 332-345, 2011.

[56] E. M. Boctor, "Medical UltraSound Imaging and Intervention Collaboration (MUSiiC) Lab Research," https://musiic.lcsr.jhu.edu/Research,

[57] R. H. Taylor, "Computer Integrated Interventional Systems (CiiS) Lab Research," http://ciis.lcsr.jhu.edu/dokuwiki/doku.php?id=research,

[58] H. J. Kang, P. J. Stolka, and E. M. Boctor, "OpenITGLinkMUSiiC: A Standard Communications Protocol for Advanced Ultrasound Research", *The MIDAS Journal*, 2011.

[59] H.-J. Kang, N. P. Deshmukh, P. Stolka, E. C. Burdette, and E. M. Boctor, "Ultrasound Imaging Software Framework for Real-Time Monitoring of Acoustic Ablation Therapy", in *SPIE Medical Imaging*, San Diego, 2012

[60] B. Vagvolgyi, S. Dimaio, A. Deguet, P. Kazanzides, R. Kumar, C. Hasser, and R. Taylor, "The Surgical Assistant Workstation", in 2008 MICCAI Workshop—Systems and Architectures for Computer Assisted Interventions, New York, Sep. 6, 2008. p. in electronic proceedings at http://midasjournal.org/browse/publication/295.

[61] B. Vagvolgyi, Li-Ming Su, R. Taylor, and G. D. Hager, "Video to CT Registration for Image Overlay on Solid Organs", in 4th Workshop on Aubmented Environments for Medical Imaging and Computer-Aided Surgery, Sep. 10, 2008.

[62] P. Kazanzides, S. DiMaio, A. Deguet, B. Vagvolgyi, M. Balicki, C. Schneider, R. Kumar, A. Jog, B. Itkowitz, C. Hasser, and R. Taylor, "The Surgical Assistant Workstation (SAW) in Minimally-Invasive Surgery and Microsurgery", in International Workshop on Systems and Architectures for Computer Assisted Interventions, Beijing, Sep. 24, 2010.

[63] G. Hager and K. Toyama., "The XVision System: A General-Purpose Substrate for Portable Real-Time Vision

[64] K. S. Arun, T. S. Huang, and S. D. Blostein, "Least-Squares Fitting of Two 3-D Point Sets", *IEEE Transactions on Pattern Analysis and Machine Intelligence*, vol. 9-5, pp. 698-700, 1987.

[65] B. K. P. Horn, H. M. Hilden, and S. Negandaripour, "Closed-form solution of absolute orientation using orthonormal matrices", *J Optical Cos Am*, vol. 5-, pp. 1127-1135, 1988.

[66] P. J. Besl and N. D. McKay, "A Method for Registration of 3-D Shapes", *IEEE Transactions on Pattern Analysis and Machine Intelligence*, vol. 14-2, pp. pp 239-256, 1992.

[67] A. Myronenko and X. Song, "Point-Set Registration: Coherent Point Drift", *IEEE Trans. on Pattern Analysis and Machine Intelligence*, vol. 32-12, pp. 2262-2275, 2010.

[68] H. Bopp and H. Krauss, "An Orientation and Calibration Method for Non-Topographic Applications", *Photogrammetric Engineering and Remote Sensing*, vol. 44-9, pp. 1191-1196, September, 1978.

[69] R. M. J. H. Haralick, "2D-3D pose estimation", in Int Conf on Pattern Recognition (ICPR), Nov. 14-17, 1988. pp. 385-391.

[70] R. Y. Tsai, "A Versatile Camera Calibration Technique for High-Accuracy 3D Machine Vision Metrology Using Off-the-Shelf TV Cameras and Lenses", *IEEE Journal of Robotics and Automation*, vol. 3-4, pp. 323-358, 1987.

[71] U.S. Pat. No. 5,551,429, J. M. Fitzpatrick and J. J. McCrory, "Method for relating the data of an image space to physical space", Filed September 3, Issue date Dec. 8, 1993 (CIP from Feb. 12, 1993).

[72] C. Maurer, M. Fitzpatrick, R. Galloway, M. Wang, R. Maciunas, and G. Allen, "The Accuracy of Image Guided Neurosurgery Using Implantable Fiducial Markers", in *Computer Assisted Radiology*, Berlin, 1995, pp. 1197-1202

[73] K. Valluru, B. Chinni, and N. Rao, "Photoacoustic Imaging: Opening New Frontiers in Medical Imaging", *Journal of Clinical Imaging Science*, vol. 1-2, pp. 1-7, 2011.

[74] J. L. Su, B. Wang, and S. Y. Emelianov, "Photoacoustic imaging of coronary artery stents", *Optics Express*, vol. 17-22, pp. 19894-19901, 2009.

[75] C. Kim, T. N. Erpelding, K. Maslov, L. Jankovic, W. J. Akers, L. Song, S. Achilefu, J. A. Margenthaler, M. D. Pashley, and L. V. Wang, "Handheld array-based photoacoustic probe for guiding needle biopsy of sentinel lymph nodes", *Journal of Biomedical Optics*, vol. 154-, p. 046010, July/August, 2010.

[76] M. G. v. Vledder, E. M. Boctor, L. R. Assumpcao, H. Rivaz, P. Foroughi, G. D. Hager, U. M. Hamper, T. M. Pawlik, and M. A. Choti, "Intra-operative ultrasound elasticity imaging for monitoring of hepatic tumour thermal ablation", *HPB (Oxford)*, vol. 12-10, pp. 717-723, December, 2010.

Example 2

In this example, we present direct 3D US to video registration and demonstrate its feasibility on ex vivo tissue. We use a 3D US transducer instead of a 2D US transducer to detect the PA signal. Using a 3D transducer allows this registration method to function for a non-planar set of 3D points. This can be a significant advantage for a laparoscopic environment. Also, organ surfaces will rarely form a planar surface. In addition to using a synthetic phantom with excellent light absorption characteristics, we also use a piece of resected ex vivo porcine liver tissue embedded in a gelatin phantom to demonstrate this method in a practical environment for applications to laparoscopic tumor resections, for example.

This example will detail the experimental procedure and algorithms to validate this method on a synthetic phantom and an ex vivo liver phantom using a 3D US transducer. We will present target registration error (TRE) results.

Methods

To perform our experiment, we use a Q-switched neodymium-doped yttrium aluminum garnet (Nd:YAG), Brilliant (Quantel Laser, France) laser frequency doubled to 532 nm wavelength at approximately 6 mJ/cm$^2$ to generate a PA effect on the synthetic phantom and approximately 19 mJ/cm$^2$ on the ex vivo tissue phantom. At this wavelength, most of the laser energy is absorbed at the superficial surface of the tissue. However, there is slight penetration into the tissue, creating a source of error that will be discussed. Our stated energy is lower than the maximum permissible exposure of 19.5 mJ/cm$^2$ as calculated from the IEC 60825-1 laser safety standard [14] based on a 0.25 s exposure time, a 4 ns pulse width, and a frequency of 10 Hz. Alternate tests showed that a lower energy was also able to generate a PA effect on ex vivo tissue. We use a SonixCEP US system along with a 4DL14-5/38 US transducer developed by Ultrasonix Medical Corporation (Richmond, Canada) to scan the volume of interest. The motor actuation of this transducer induces angular movement around an internal pivot point. The Sonix DAQ device, developed in collaboration between the University of Hong Kong and Ultrasonix, and the MUSiiC toolkit [15] is used to acquire pre-beam-formed radiofrequency (RF) data directly from the US machine. We use the k-wave toolbox[16] in MATLAB (Mathworks Inc. Natick, Mass.) designed for reconstructing PA images based on RF data. A custom-built SC system containing two CMLN-13S2C cameras (Point Grey Research, Richmond, Canada) is used to capture images to be used for 3D triangulation. The synthetic phantom is made using plastisol and black dye. The ex vivo liver phantom is made using a gelatin solution and a freshly resected porcine liver. The surface of the liver is partially exposed and not covered by gelatin. Alternate tests with other surfaces such as porcine kidney tissue and fat were also successful in generating a PA signal.

Figure 10B:
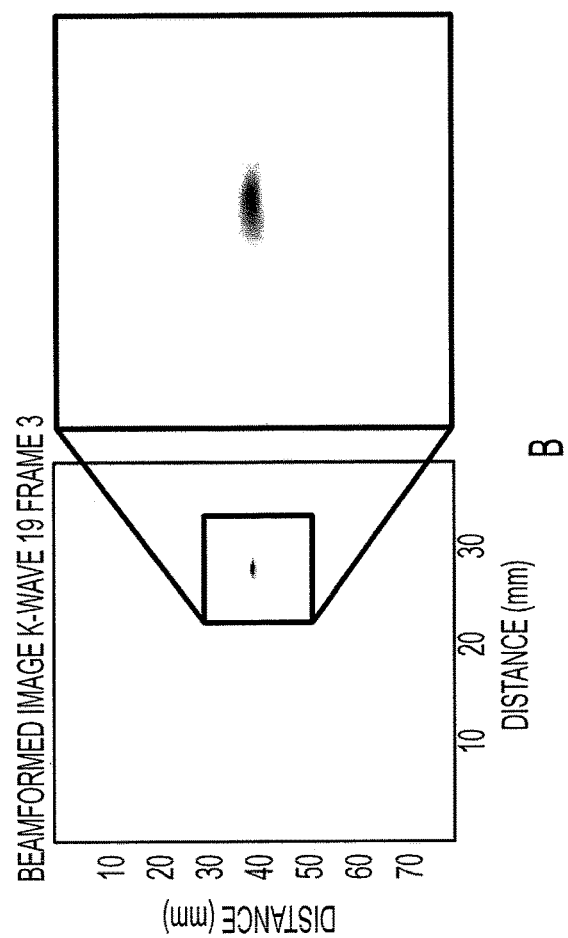
FIGS. 10A and 10B shows A) Experimental Setup and Video Overlay, B) PA Signal within an US image.
Figure 10A:
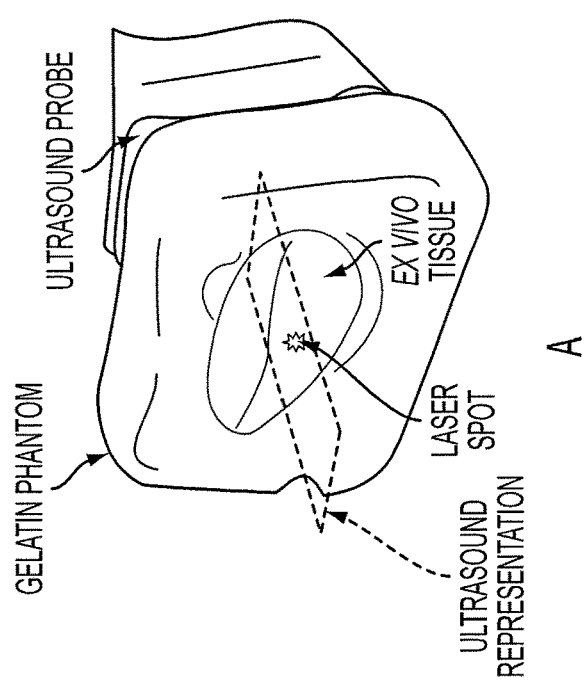

Our experiment can be split into a data collection phase and a data processing phase. The data collection phase outputs SC image pairs, five frames for each camera, and a 3D RF US volume for each projected laser spot. The number of frames is arbitrary. The data processing phase uses the data and generates a coordinate transformation from the SC frame to the US frame. FIG. 10A shows the experimental setup and an overlay of a US image representation using the inverse of the transformation.

Figures 11A, 11B, 11C:
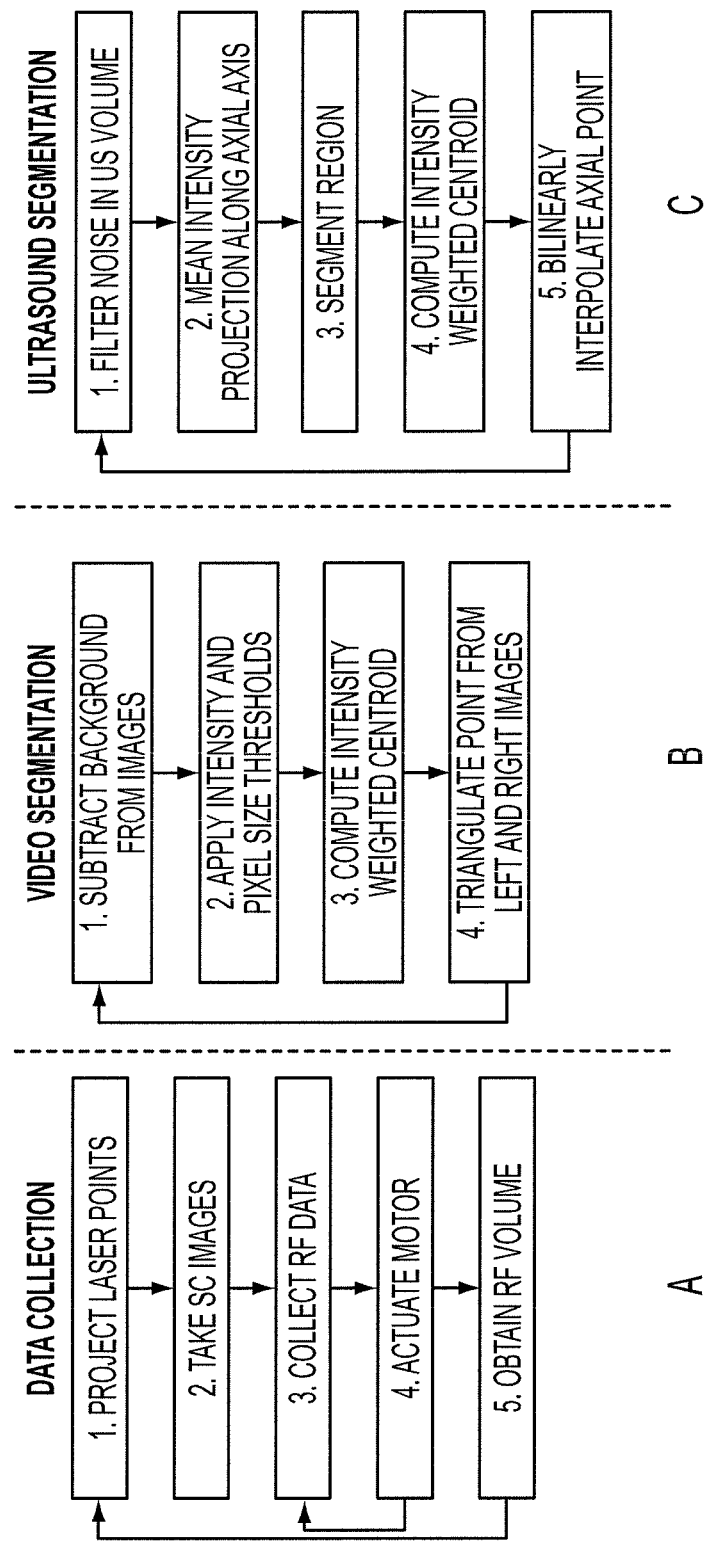
FIGS. 11A-11C show workflow for A) Data Collection, B) SC Segmentation, and C) US Segmentation.

FIG. 11A shows the workflow of the data collection phase. First a laser spot is projected onto the exposed surface of the ex vivo liver phantom. There will be inaccuracies in SC spot triangulation if the laser spot is projected at or near the liver gelatin interface because the laser spots become irregularly shaped when projected onto clear materials. Second, several images are taken for each camera. The laser spot projected onto the phantom must be visible in at least one image per camera for triangulation to be possible. Our cameras have a faster capture rate than our laser's repetition rate, so some of the frames will be devoid of the laser signal. We will exploit this during data processing. Steps 3 and 4 show that the 3D US transducer motor actuation and RF data are intermittently collected from the DAQ device to scan and acquire the RF data of the volume of interest. The volume's field of view is 14.7° for the ex vivo tissue phantom, 19.6° for the synthetic phantom and the motor step size is 0.49°. This iterative process is manual, but an automatic process is in development. This workflow is repeated for each of the thirty laser spots.

The data processing phase involves the segmentation of the SC images into 3D SC points, the segmentation of the 3D RF US volume data into 3D US points, and the computation of the transformation from the SC frame to the US frame.

FIG. 11B shows the workflow for SC segmentation. For each camera, we pick a SC image with the laser spot and without the laser spot. Next, the background images without the laser spot are subtracted from the images with the laser spot. This step makes it significantly easier to segment the laser spot. We then apply an appropriate intensity and pixel size thresholds such that the laser spot is segmented out. These thresholds are selected based on the laser beam diameter and the phantom's reflectance. Next, we fit an ellipse to the segmented region and compute the intensity weighted centroid. Calibration files for our specific SC allow us to triangulate the segmented point from each camera and obtain a single 3D point in the SC frame. This workflow is repeated for each laser spot projection. We use thirty sets of SC images.

The workflow for the segmentation of the 3D RF US volume is shown in FIG. 11C. First, for each slice of a 3D RF US volume, the RF data is beamformed using the k-wave toolbox[16] in MATLAB. The dynamic range of the image is normalized with respect to the volume to decrease the size of the PA signal seen in each volume. FIG. 10B shows the k-wave beamformed PA signal image. Next, we project the volume onto the lateral-elevational plane by taking the mean along each axial ray. An appropriate intensity and pixel size threshold is then applied to this image. An ellipse is fitted on the segmented region and an intensity-weighted centroid is computed resulting in lateral and elevational coordinates. As described earlier, the PA signal originates from the surface and any penetration into the surface. Since air cannot generate a PA signal in our setup, we can exploit that the high intensity pixels farthest away in the axial direction are from the surface. Thus, we obtain the axial coordinate corresponding with a lateral-elevational coordinate as the axial-most high intensity pixel. This step is particularly important because the penetration of the laser pulse is much deeper for the ex vivo tissue phantom than the penetration for the synthetic phantom. We use bilinear interpolation to obtain axial coordinates between sampled points. These three coordinates are converted to 3D US coordinates based on transducer specifications. This workflow is repeated for each of our thirty 3D RF US volumes.

The transformation from the SC frame to the US frame can be computed with the 3D SC and 3D US point sets. Any registration method for computing the transformation between two 3D point sets can be used. We use the coherent point drift algorithm [17] in our experiment. One of the main reasons for using coherent point drift is that it allows for data points to be missing from either dataset. An assumption that we have made is that each laser spot will be visible in the SC images and each PA signal will be visible in the US volume. This assumption is valid for our experiment, but may not hold in the surgical setting due to SC or transducer movement. The coherent point drift registration algorithm allows us to acquire a registration as long as there are enough corresponding points in the SC images and the US volume.

The transformation from the SC frame to the US frame is used to transform the 3D SC points to the US frame for validation. The inverse transformation is used to display a representation of an US image into the SC frame as shown in FIG. 10A.

Results

The results of our experiment on the synthetic phantom and on the ex vivo tissue phantom are validated using the target registration error (TRE) metric defined in equation 1. $F_{SC\_US}$ is the transformation from the SC frame to the US frame and is computed with all of SC and US points except for one. The TRE is the resulting difference between the actual US test point and the transformed SC test point in the US frame.

$$\vec{TRE} = F_{SC\_US} * \vec{SC}_{test} - \vec{US}_{test} \quad (1)$$

Twenty-nine of the thirty points are used to compute the transformation from the SC frame to the US frame. The remaining point is used as a test point to compute the TRE. This computation is repeated with each of the thirty points as test points. Table 1 shows the average and standard deviation of the TRE results for the thirty cases in the synthetic phantom and the ex vivo tissue phantom experiment respectively.

TABLE 1

Average TRE Results for Leave One Out Registration Experiments

| n = 30 | Synthetic Phantom | Ex vivo Tissue Phantom |
|---|---|---|
| Lateral (mm) | 0.21 ± 0.17 | 0.22 ± 0.16 |
| Axial (mm) | 0.21 ± 0.13 | 0.24 ± 0.15 |
| Elevational (mm) | 0.41 ± 0.31 | 0.18 ± 0.10 |
| Euclidean Norm (mm) | 0.56 ± 0.28 | 0.42 ± 0.15 |

Discussion

There are several considerations when discussing this system's deployment in applications of laparoscopic tumor resections. The first is the placement of the transducer. In our experiments, we use a relatively large 3D US transducer that would be near impossible to put inside the body during a laparoscopic procedure. However, the transducer is often placed externally [3], [8] in these procedures, so the size of the probe is not an issue. Naturally, there are disadvantages of placing the transducer externally and farther from the region or organ of interest. The quality of ultrasound images degrades as the depth increases, which would likely lead to errors in localizing fiducials or, in our case, the PA signal. However, since the PA signal only has to travel in one direction, as opposed to traditional US, our PA images will have better quality than US images of equivalent depth.

Another issue with our 3D US transducer is the acquisition speed. There are certain applications where an acquisition speed of a volume per several seconds is sufficient, but a real-time implementation would require a higher acquisition rate. In some embodiments, 2D array US transducers for a real-time implementation can be used. These transducers can provide an acquisition rate on the order of twenty volumes per second. The 2D array transducer can also be miniaturized and placed closer to the region of interest.

A third issue deals with the laser delivery system. As shown in our experimental setup, a laser would have to be fired at the organ in free space. This occurrence is unlikely in practical situations. A fiber delivery tool can be used that will allow us to safely guide the laser beam into the patient's body. This tool can also be able to project concurrent laser spots, greatly enhancing our registration acquisition rate.

At the level of error measurements shown in Table 1, it is likely that the calibration of the SC system is a significant contributor. They are able to locate point sources at sub-millimeter accuracy [6], [7]. This error is usually negligible in comparison with the 3 mm errors from calibration. Since our results are 0.56 mm and 0.42 mm errors respectively, the SC system's error becomes significant. We use a custom SC system, so its errors are likely greater than a finely tuned commercial SC system.

The experimental results in Table 1 show that our system achieves sub-millimeter TRE measurements for both the synthetic phantom and the ex vivo tissue phantom. There is a slight difference in the results, and it is entirely due to the elevational error. This is likely due to the larger field of view in the synthetic phantom experiment as well as normal variation across experiments.

There are a couple of factors that affect these errors as we move from a bench-top setup to in vivo. When our SC system is replaced with a stereo endoscopic camera, the errors may increase. This is because our SC system has a larger disparity than standard stereo endoscopic cameras. Also, the errors are reported based on surface points. Since the region of interest is often subsurface, our reported TRE will be biased for subsurface target errors. We believe that the bias will be fairly small since the PA spots are being detected in the same modality as any subsurface regions.

REFERENCES FOR EXAMPLE 2

1. Wang Y., Butner S., and Darzi A.: The developing market for medical robotics. Proceedings of the IEEE 94(9), 1763-1771, September (2006).
2. Taylor, R., Lavallee, S., Burdea, G., and Mosges, R.: Computer integrated surgery. MIT Press Cambridge, Mass. (1996).
3. Stolka P. J., Keil M., Sakas G., McVeigh E., Allaf M. E., Taylor R. H., and Boctor E. M.: A 3D-elastography-guided system for laparoscopic partial nephrectomies. in Medical Imaging 2010: Visualization, Image-Guided Procedures, and Modeling, San Diego, February 13-18, 76251I, 76251I-12 (2010)
4. Boctor E., Viswanathan A., Choti M., Taylor R., Fichtinger G., and Hager G.: A Novel Closed Form Solution for Ultrasound Calibration. in International Symposium on Biomedical Imaging, Arlington, 527-530 (2004)
5. Poon T. and Rohling R.: Comparison of calibration methods for spatial tracking of a 3-D ultrasound probe. Ultrasound in Medicine and Biology 31(8), 1095-1108, August (2005)
6. Navab N., Mitschke M., and Schutz O.: Camera-Augmented Mobile C-Arm (CAMC) Application: 3D Reconstruction using Low Cost Mobile C-Arm. in MICCAI 1999, 688-697 (1999)
7. Wiles A., Thompson D., and Frantz D.: Accuracy assessment and interpretation for optical tracking systems. Proceedings of SPIE, 5367, 421-432 (2004)
8. Yip M. C., Adebar T K., Rohling R., Salcudean S. E., and Nguan C. Y.: 3D Ultrasound to Stereoscopic Camera Registration through an Air-Tissue Boundary. in *MICCAI* 2010 2, 626-634 (2010)
9. Vyas S., Su S., Kim R., Kuo N., Taylor R. H., Kang J. U., and Boctor E.: Interoperative Ultrasound to Stereo-camera Registration using Interventional Photoacoustic Imaging. in Medical Imaging 2012: Visualization, Image-Guided Procedures, and Modeling, San Diego, February 4-9, 8316, 83160S (2012)
10. Kolkman R., Steenbergen, W., and van Leeuwen T.: In vivo photoacoustic imaging of blood vessels with a pulsed laser diode. Lasers in medical science 21(3), 134-139 (2006).
11. Kuo N., Kang H. J., DeJournett T., Spicer J., and Boctor E. M.: Photoacoustic imaging of prostate brachytherapy seeds in ex vivo prostate. in Medical Imaging 2011: Visualization, Image-Guided Procedures, and Modeling, Lake Buena Vista, February 12-17, 7964, 796409 (2011)
12. Xu M. and Wang L.: Photoacoustic imaging in biomedicine. Review of scientific instruments 77, 041101 (2006)
13. Hoelen C., De Mul F., Pongers R., and Dekker A.: Three-dimensional photoacoustic imaging of blood vessels in tissue. Optics letters 23(8), 648-650 (1998)
14. IEC 60825-1:1993+A1:1997+A2:2001: Safety of Laser Products—Part 1: Equipment Classification and Requirements. International Electrotechnical Commission, Geneva (2001)
15. Kang H. J., Kuo N., Guo X., Song D., Kang J. U., and Boctor E. M.: Software framework of a real-time pre-beamformed RF data acquisition of an ultrasound research scanner. in Medical Imaging 2012: Visualization, Image-Guided Procedures, and Modeling, San Diego, February 4-9, 8320, 83201F (2012)
16. Treeby B., and Cox B.: k-Wave: MATLAB toolbox for the simulation and reconstruction of photoacoustic wavefields. *Journal of Biomedical Optics* 15(2), 021314 (2010)
17. Myronenko A., and Song X.: Point-Set Registration: Coherent Point Drift. IEEE Trans. on Pattern Analysis and Machine Intelligence 32(12), 2262-2275 (2010)

Example 3

In this example we refine and evaluate the registration required to bring the preoperative prostate MRI model into the da Vinci visualization system. To achieve this goal we perform the following three tasks to be executed in the following order:

Task 1:

3DUS B-mode and PA-mode reconstruction

Rationale:

Volumetric intraoperative ultrasound is used to fuse the pre-operative MRI model to the surgical scene. In general, 3DUS data can be acquired using two different approaches. One approach is to utilize a 2D ultrasound array to directly provide 3DUS B-mode data. Unfortunately, these 2D arrays are not widely available and to the best of our knowledge, there is no 2D TRUS array. Alternatively, there are a number of mechanical probes that provide 3DUS data by wobbling a 1D array, but these are relatively slow and need customization to synchronize with a PA imaging system. The second approach is to track a conventional 1D TRUS probe using mechanical, optical or electromagnetic tracking devices. In our previous work, we integrated an EM tracker into a laparoscopic and robotic environment to guide partial nephrectomy procedures [Stolka-2009,-2010] and faced the following challenges: 1) the need for calibration between the US image reference frame and the tracking sensor reference frame; 2) interference with EM trackers (or line-of-sight issues with optical trackers), especially in the robotic environment; 3) the intrusiveness and bulkiness of these trackers as we need to integrate a base station (field generator for EM or cameras for optical); and 4) an overall navigation accuracy of 3-5 mm, which is not sufficient to navigate critical structures in prostatectomy procedures.

Figure 12:
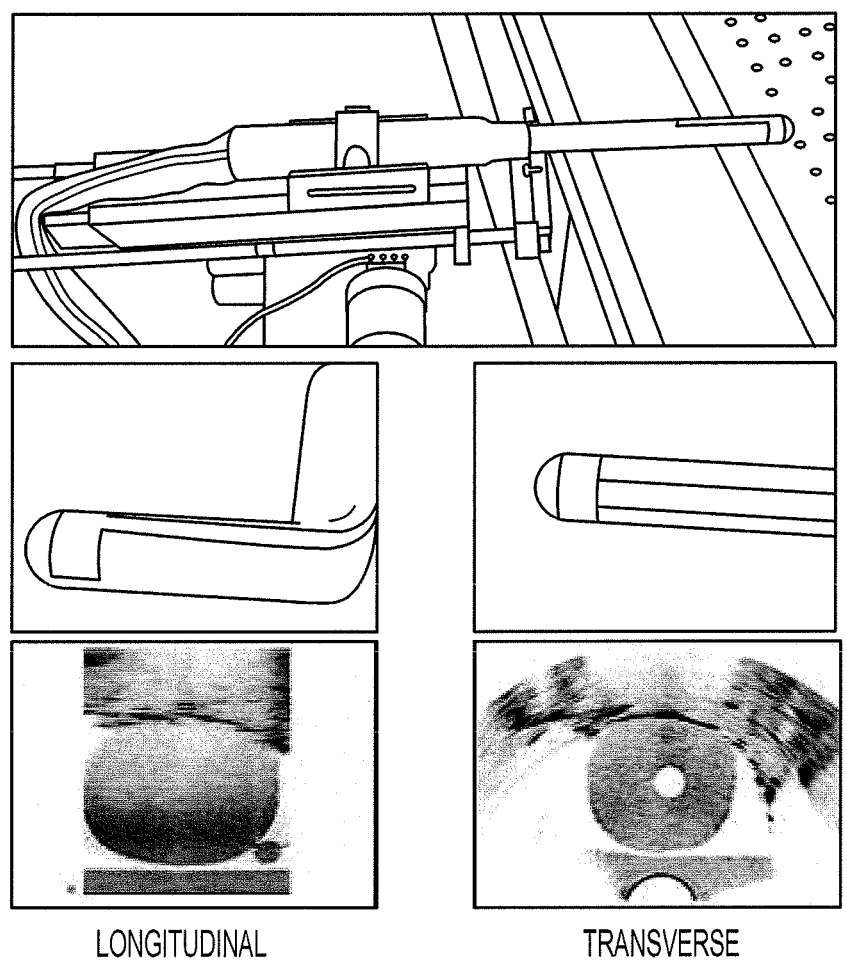
FIG. 12 shows a typical imaging configuration of the dual-array TRUS probe.

Our approach is to utilize a readily available dual-array TRUS probe [Ultrasonix BPC8-4/10 or BCPL9-5/55]. These arrays provide two orthogonal views in real-time: a linear array provides a longitudinal section and convex array provides a transverse section, as shown in FIG. 12. We reconstruct a 3DUS volume by rotating the probe around its main axis and incrementally collecting images from the linear (longitudinal) array. In this motion scenario, the convex (transverse) array images will exhibit in-plane motion (3 degrees of freedom) that tracks rotational sweep. It is important to note that both arrays can be utilized for recovering tracking information. If a small translational motion is introduced while rotating the probe about its axis, the convex array will not detect out-of-plane motion. However, the linear array image sequence will easily detect it.

Methodology:

For any given image from the convex array, the first step is to find a few "leading points" or feature points inside the image. Given two images, a cost function is defined for specific in-plane degrees of freedom (lateral translation, axial translation, and elevational rotation). These are all global motion parameters defined as a scalar for the whole image. To compute the cost function, a simple block matching using NCC can be performed. The key is that the block matching only happens for the selected leading point and not for the whole image, which makes it fast and robust. The incoming images are matched with a reference image that does not change until the rotation/translation in the image reaches a certain threshold. At this point, the reference is switched to a new image. If the tracking is lost, the algorithm goes to a recovery mode which down-samples the images and searches the whole image to match the images. Because of down-sampling it is not accurate, but accuracy is restored when the algorithm switches back to normal tracking mode. The JHU group has recently demonstrated a similar method to stitch US images to compose a panoramic view for an entire forearm. In this application, we do not expect this extreme motion.

With freehand acquisition, the probe motion will be more than one rotational degree-of-freedom. The proposed image-based approach can still handle this complex motion by extending our tracking algorithm to utilize both orthogonal arrays' imaging data. Our team has extensive experience in dealing with probe tracking using a single probe/array and relying on fully-developed speckle features. We do not expect to face this problem here because the freehand acquisition will be guided by a stage similar to the one shown in FIG. 12. Alternatively, we can easily track 6 DoF motion by utilizing the PA-based tracking approach described in Task 2.

Task 2:

Multi-modality fusion utilizing photoacoustic imaging data

Rationale:

Transrectal ultrasound (TRUS) has emerged as the intraoperative imaging modality of choice for radical prostatectomy. Studies have demonstrated that it can help identify prostate margins. An AR navigation system that directly fuses stereo video with tracked 3D TRUS volume has been proposed for prostatectomy. By directly utilizing the intraoperative imaging modality, the system avoids the complication of deformable registration. But, due to its relatively low resolution and signal-to-noise ratio, TRUS is not ideal for detecting critical detailed surrounding anatomies such as the neurovascular bundles. On the other hand, MR scans provide clear delineation of intraprostatic and surrounding anatomies, but become deregistered immediately after the patient is removed from the MR scan table. By extracting detailed MR models and aligning them with intra-operative TRUS that is tracked within the da Vinci system, we can overlay the models on top of the live stereo video and provide surgeons with an X-ray vision of critical anatomies.

Methodology:

Before we describe our registration approach, we will detail our intraoperative data acquisition. Task 1 describes the ability to acquire 3DUS data using an available bi-plane TRUS probe. These data include conventional B-mode imaging, which is essential to reveal prostate anatomy and boundary, and PA-mode imaging, which can reveal small vascular structures that cannot be recovered using conventional Doppler imaging. Both prostate anatomy and vascular structures are essential to perform reliable deformable registration with pre-operative MRI. PA imaging is developed based on the photoacoustic effect, originally described by Alexander Graham Bell who showed that thin discs produced sound when exposed to an interrupted beam of sunlight. In PA imaging an object is usually irradiated by a short-pulsed, non-ionizing laser beam. Some of the delivered energy is absorbed, according to optical absorption properties of biological tissue, and converted into heat, leading to transient thermoelastic expansion and thus wide-band ultrasonic emission. The generated ultrasonic waves are detected by ultrasonic transducers to form images. It is known that optical absorption is closely associated with physiological properties, such as hemoglobin concentration and oxygen saturation. As a result, the magnitude of the ultrasonic emission (i.e. photoacoustic signal), which is proportional to the local energy deposition, reveals physiologically specific optical absorption contrast.

Figure 13:
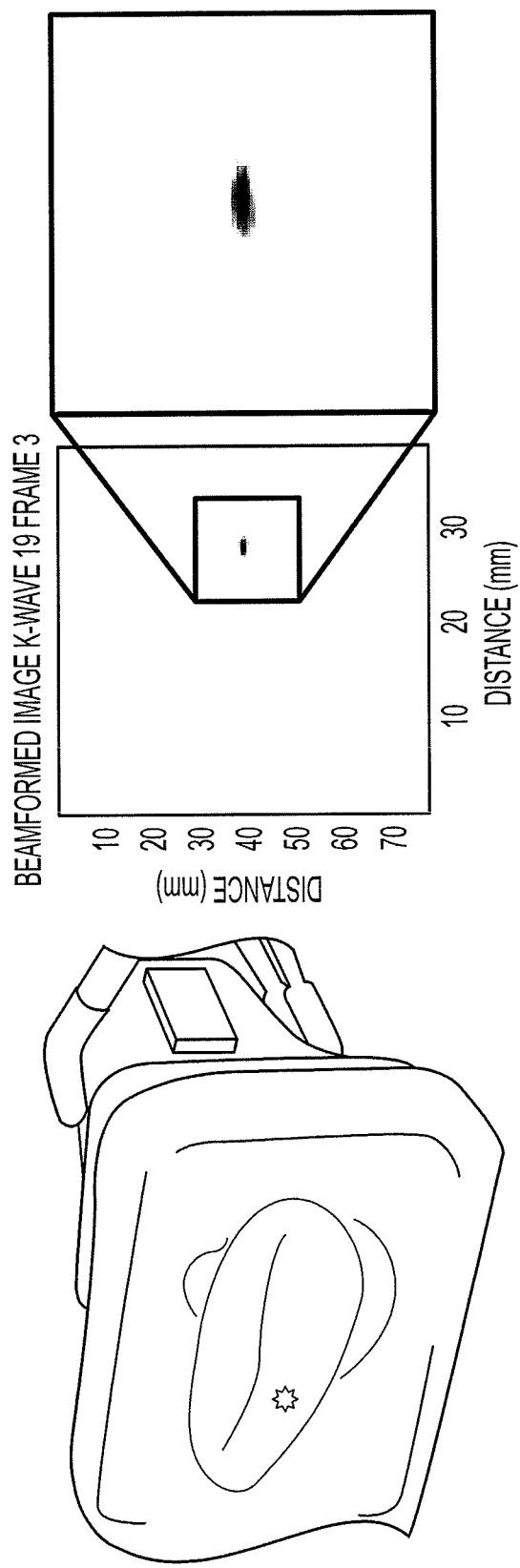
FIG. 13 shows photoacoustic tracking feasibility study: (left) Photograph of a scanned laser, US and stereo camera setup, in a typical trial. (middle, right) PA image reconstructed from pseudo-spectra analysis and k-space Green's function method for one spot.
Figure 14:
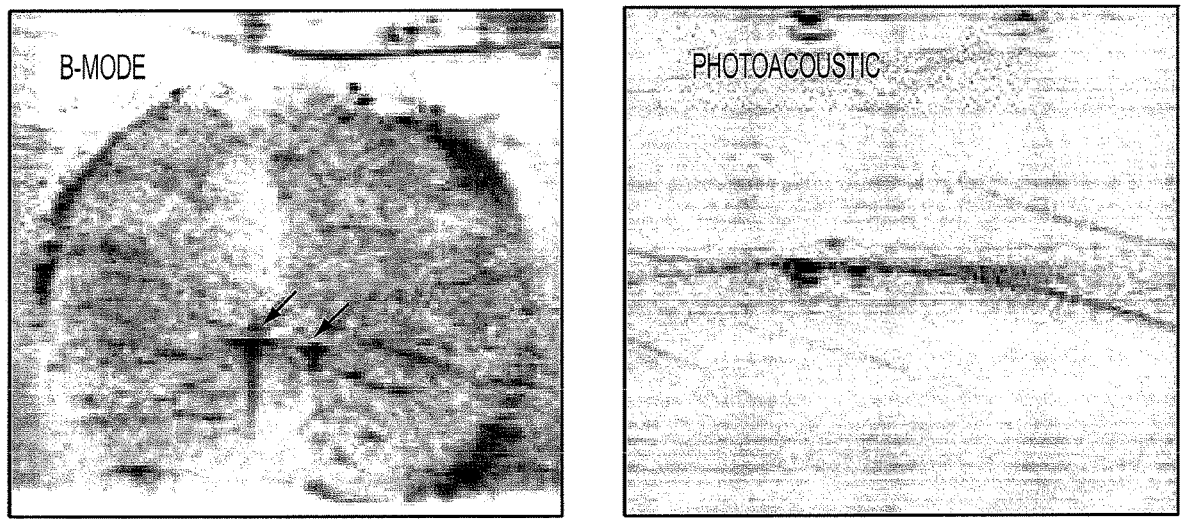
FIG. 14 shows visualization of brachytherapy seeds in ex-vivo dog prostate using system.
Figure 15:
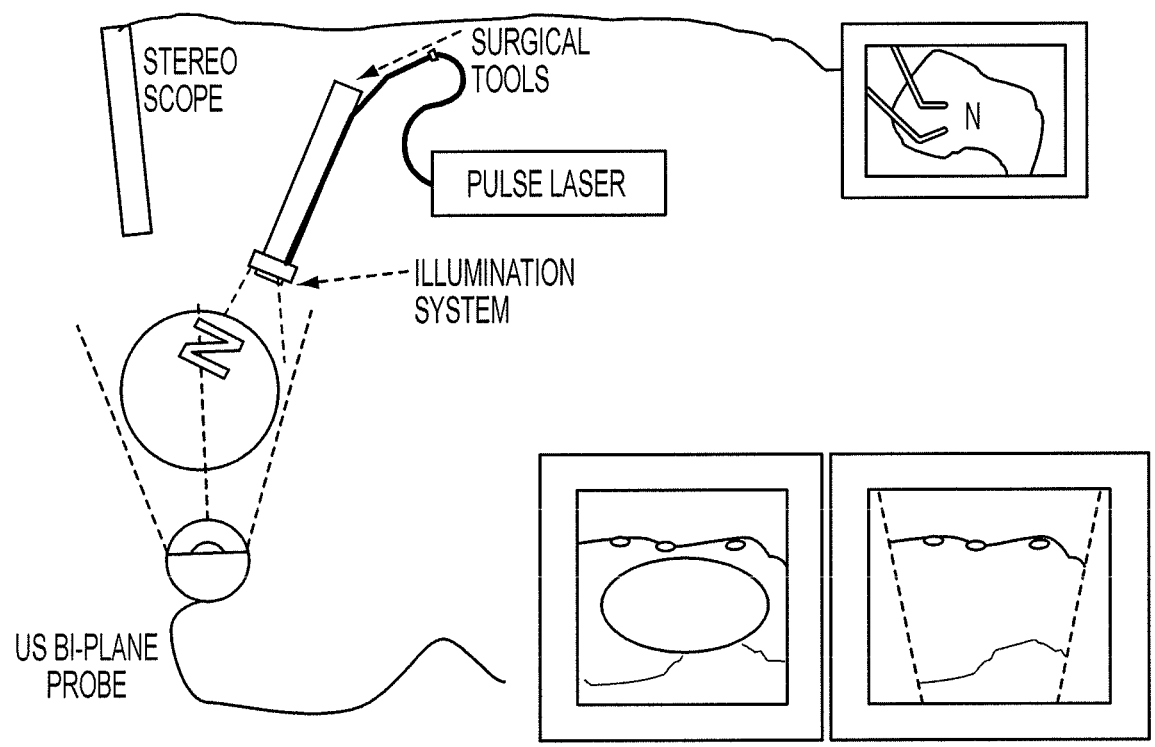
FIG. 15 is a schematic illustration of an intraoperative registration and tracking system according to an embodiment of the current invention.

We have demonstrated the use of the photoacoustic (PA) effect to register 3D ultrasound images to 3D video images (see FIG. 13). Dr. Boctor has also conducted experiments to detect Brachytherapy seeds based on PA imaging. This has demonstrated accurate, high-contrast PA imaging and localization of brachytherapy seeds in ex-vivo dog prostate using 1064 nm laser pulses (see FIG. 14). The system (FIG. 15) includes: 1) a laser illumination system; 2) a dual-array TRUS probe; and 3) a da Vinci endoscope. The illumination system will direct a "Z" or "N" pattern of laser pulses onto the surface of prostate organ within the field of view of the endoscope. It may be mounted with the camera or may be held by one of the da Vinci instruments, so long as it shines these patterns where they are visible from the endoscope. The pattern can be produced through the following design alternatives: a) multiple optical fibers to shape the pattern; b) a relatively large fiber (1-2 mm in diameter) with a lens and aperture to produce the pattern; and 3) a single small fiber (200 um diameter) that can be actuated by small motors to produce the pattern. Energy absorbed from the pulsed laser spots will generate PA signals that may be imaged by the ultrasound system, thus creating a pattern of "virtual" surface "Z" fiducial marker. Because the selected wavelength (532 nm) of these laser patterns is visible at all times in the endoscope, the registration between video and ultrasound coordinate systems is a straightforward process [Cheng-2012]. Since the ultrasound images can concurrently locate prostate anatomy, registration and tracking of preoperative MRI images relative to the video coordinate system may likewise be accomplished. The laser illumination system can target a relatively larger field-of-view with wavelengths (700-800 nm) to generate PA images of the neuro-vascular bundle which will be utilized, with the B-mode information, to perform multimodality registration.

Our current Q-switched laser has two main wavelength outputs (1064 nm and the frequency doubled 532 nm output) and tunable output from the OPO unit (690-950 nm). The 532 nm laser light is green in color and can produce a strong photoacoustic signal since it is strongly absorbed by the soft tissues and blood, typical of most surgeries. 1064 nm light has greater penetration depth than the 532 nm light. This is mainly because both Hb and HbO2 have less optical absorption coefficient at 1064 nm compared to 532 nm. In fact, Hb compared to HbO2 has a relatively higher optical absorption coefficient in the range of 650 nm-750 nm. For surface laser spots and for tracking tasks we will use 532 nm. With our recent PA experiments utilizing kidney, liver [Cheng-2012] and fat, we have shown that 532 nm generates PA signals at the tissue-air interface. For PA vascular imaging and for initial multi-modality fusion of US/PA with preoperative MRI, we will investigate the use of the following wavelength 532 nm and the range of 690-750 nm. We will also explore and investigate the use of low-cost pulsed laser diodes (PLD). Some results indicate that we can get usable PA surface images in phantoms with 2-16 uJ pulses, comparable to energy from available PLDs.

Other embodiments are not limited to the examples and embodiments described above. For example, in another embodiment of this invention, a single "one dimensional" ultrasound sensor may be deployed on the end of a catheter or probe inserted into an organ and used to determine the distances to multiple spots on the surface of the organ. This information may be used to determine the 3D position of the sensor relative to the spots and hence to the optical imaging system.

In another embodiment, optical illumination and the generated pattern can be two separate events. As described above, photoacoustic tracking according to some embodiments of the current invention is to generate several fiducial landmarks (spots or patterns) that can be observed by the camera (single, stereo, or more than two) and also can be detected by the ultrasound sensing system. Hence, a spatial relationship between the ultrasound sensor and the camera system can be calculated from matching these features in both spaces. These features or patterns can be generated by the same illumination system. For example, one can use multiple fibers to generate a random pattern of several non-collinear spots as shown in [Cheng-2012] and FIG. 2, for example. This pattern can also be of "Z" or "N" shape, where the ultrasound image can intersect in few points—typically three across this "Z" shape. In addition, the pattern can be generated physically. This means that the surgeon can paint a pattern right on top of the surgical site or suture a random "small" material to the surface to be cut. In this case, the illumination system can be simplified to generate enough flux to cover the area of interest. The physical paint or sutured fiducial marks can be made of materials that are sensitive to specific wavelength and also can provide better transduction coefficient (i.e. conversion ratio from light to sound energy). These materials can be made of black paint; or made of Polydimethylsiloxane (PDMS) mixed with Carbon black that has a coefficient of $310*10^{-6}$/K, more than ten times higher than common metals.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. An intraoperative registration and tracking system, comprising:
    an optical source configured to illuminate tissue during an intraoperative procedure with electromagnetic radiation to generate a photoacoustic affect at three or more localized spots;
    an optical imaging system configured to form an optical image of the tissue and to detect and determine a position of each of the three or more localized spots in the optical image;
    an ultrasound imaging system configured to form an ultrasound image of the tissue and to detect and determine a position of each of the three or more localized spots in the ultrasound image; and
    a registration system configured to determine a coordinate transformation that registers the optical image with the ultrasound image based at least partially on a correspondence of the three or more localized spots in the optical image with corresponding three or more localized spots in the ultrasound image,
        the registration of the optical image to the ultrasound image being updated during the intraoperative procedure.

2. The intraoperative registration and tracking system according to claim 1, wherein the registration system is configured to perform a coherent point drift algorithm for determining the coordinate transformation that registers the optical image with the ultrasound image.

3. The intraoperative registration and tracking system according to claim 1, wherein the optical source comprises a plurality of optical waveguides to selectively provide the three or more localized spots.

4. The intraoperative registration and tracking system according to claim 1, wherein the optical source comprises one or more steerable optical components to selectively provide the three or more localized spots.

5. The intraoperative registration and tracking system according to claim 1, wherein the optical imaging system comprises a stereo video camera.

6. The intraoperative registration and tracking system according to claim 1, wherein the optical source comprises a pulsed laser.

7. The intraoperative registration and tracking system according to claim 6, wherein the pulsed laser is configured to selectively emit at a primary wavelength and at a frequency doubled wavelength.

8. The intraoperative registration and tracking system according to claim 6, wherein the optical source comprises:
    an optical fiber rigidly attached relative to the optical imaging system, and
    wherein a portion of the optical imaging system and the optical fiber are configured to be inserted at least one of interstitially or laparoscopically.

9. The intraoperative registration and tracking system according to claim 8, wherein the optical source further comprises:
    at least another optical fiber rigidly attached relative to a surgical tool, the surgical tool to be at least one of registered or tracked by the intraoperative registration and tracking system.

10. The intraoperative registration and tracking system according to claim 1, further comprising:
a turret upon which at least a portion of the optical source and the optical imaging system are attached,
wherein at least one of a position or an orientation of at least a portion of the turret can be adjusted during a surgical procedure.

11. The intraoperative registration and tracking system according to claim 1, wherein the ultrasound imaging system comprises:
an ultrasound transducer that is configured to receive ultrasound signals from the optical source, and
wherein the ultrasound imaging system is configured to form the ultrasound image based on the ultrasound signals from the optical source.

12. The intraoperative registration and tracking system according to claim 1, wherein the ultrasound imaging system comprises:
an ultrasound transducer that is configured to receive ultrasound signals from the optical source and to transmit ultrasound signals, and
wherein the ultrasound imaging system is configured to form the ultrasound image based on at least one of the ultrasound signals from the optical source or the ultrasound signals that return to the ultrasound transducer after being emitted from the ultrasound transducer.

13. The intraoperative registration and tracking system according to claim 1, further comprising:
a tracking system configured to identify an object in a plurality of registered optical and ultrasound images at a corresponding plurality of times to thereby track positions of the object at each of the corresponding plurality of times.

14. The intraoperative registration and tracking system according to claim 1, wherein the optical source is further configured to provide continuous illumination to illuminate the tissue intraoperatively with light to be detected by the optical imaging system.

15. The intraoperative registration and tracking system according to claim 14, wherein the optical source comprises a continuous wave laser.

16. The intraoperative registration and tracking system according to claim 14, wherein the registration system is further configured to register preoperative images with the optical image and the ultrasound image based on fiducial markers in the tissue that are locatable in at least one of the optical image or the ultrasound image.

17. The intraoperative registration and tracking system according to claim 1, wherein the optical source is further configured to provide a safety beam of light.

18. A method, comprising:
receiving, by a device, imaging data associated with an ultrasound system,
the ultrasound system to form an ultrasound image of at least a region of interest of a patient during an intraoperative procedure,
the region of interest being illuminated during the intraoperative procedure with three or more photoacoustic sources to form three or more localized illuminated spots,
receiving, by the device, optical data associated with an optical imaging system,
the optical imaging system to form an optical image of at least the region of interest of the patient during the intraoperative procedure,
the three or more localized illuminated spots being in view of the optical imaging system and the ultrasound system during the intraoperative procedure,
the ultrasound system and optical imaging system being independently moveable with respect to each other; and
determining, by the device, a coordinate transformation that registers the optical image to the ultrasound image based at least partially on a correspondence of the three or more localized illuminated spots in the optical image to corresponding spots in the ultrasound image,
a registration of the optical image to the ultrasound image being updated during the intraoperative procedure.

19. The method of claim 18, further comprising:
identifying an object in a plurality of registered optical and ultrasound images at a corresponding plurality of times to track one or more positions of the object at each of the corresponding plurality of times.

20. A system, comprising:
an optical source configured to illuminate tissue of a patient during an intraoperative procedure with electromagnetic radiation,
the optical source to illuminate the tissue at three or more localized spots;
an optical imaging system configured to form an optical image of at least a portion of the tissue of the patient,
the optical imaging system to detect and determine a position of each of the three or more localized spots in the optical image;
an ultrasound imaging system configured to form an ultrasound image of at least the portion of the tissue of the patient,
the ultrasound imaging system to detect and determine a position of each of the three or more localized spots in the ultrasound image; and
a registration system configured to determine a coordinate transformation that registers the optical image with the ultrasound image based at least partially on a correspondence of the three or more localized spots in the optical image with corresponding three or more localized spots in the ultrasound image,
a registration of the optical image to the ultrasound image being updated based upon updated position information associated with the position of each of the three or more localized spots in the ultrasound image and the position of each of the three or more localized spots in the optical image.

21. The system of claim 20, wherein the registration system is configured to perform a coherent point drift algorithm for determining the coordinate transformation that registers the optical image with the ultrasound image.

22. The system of claim 20, further comprising:
a tracking system configured to identify an object in a plurality of registered optical and ultrasound image pairs at a corresponding plurality of times to thereby track positions of the object at each of the corresponding plurality of times.

23. The system of claim 20, wherein the optical source comprises one or more steerable optical components to selectively provide the three or more localized spots.

24. The system of claim 20, wherein the optical source further comprises:

an optical fiber rigidly attached relative to a surgical tool, the surgical tool to be at least one of registered or tracked by the system.

* * * * *